United States Patent
Lee et al.

(10) Patent No.: US 11,235,315 B2
(45) Date of Patent: Feb. 1, 2022

(54) OLIGOMERIZATION CATALYST AND METHOD FOR PREPARING ETHYLENE OLIGOMER USING SAME

(71) Applicants: SK Innovation Co., Ltd., Seoul (KR); SK Global Chemical Co., Ltd., Seoul (KR)

(72) Inventors: Sang Ick Lee, Daejeon (KR); Eun Jung Baek, Daejeon (KR); Sun Young Kim, Daejeon (KR); Hyo Seung Park, Daejeon (KR); Min Seon Jung, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 144 days.

(21) Appl. No.: 16/300,973

(22) PCT Filed: May 11, 2017

(86) PCT No.: PCT/KR2017/004849
§ 371 (c)(1),
(2) Date: Nov. 13, 2018

(87) PCT Pub. No.: WO2017/204476
PCT Pub. Date: Nov. 30, 2017

(65) Prior Publication Data
US 2019/0308178 A1 Oct. 10, 2019

(30) Foreign Application Priority Data
May 27, 2016 (KR) .................. 10-2016-0065709

(51) Int. Cl.
*B01J 31/18* (2006.01)
*B01J 31/14* (2006.01)
(Continued)

(52) U.S. Cl.
CPC .......... *B01J 31/181* (2013.01); *B01J 31/143* (2013.01); *B01J 31/223* (2013.01);
(Continued)

(58) Field of Classification Search
None
See application file for complete search history.

(56) References Cited

U.S. PATENT DOCUMENTS 4,069,273 A 1/1978 Komoto
6,800,702 B2 10/2004 Wass
(Continued)

FOREIGN PATENT DOCUMENTS

CA 2278572 A1 * 7/1998 .............. B01J 31/24
CN 104086350 A * 10/2014
(Continued)

OTHER PUBLICATIONS

Ittel et al. (Inorganic Chemistry, 16(5), 1977, 1245-1246 (Year: 1977).*
(Continued)

*Primary Examiner* — Yun Qian
(74) *Attorney, Agent, or Firm* — The Webb Law Firm

(57) ABSTRACT

The present invention relates to an oligomerization catalyst including a transition metal or transition metal precursor, a halogen-substituted organic ligand, and a heteroatom ligand, and to a method for selectively preparing 1-hexene or 1-octene from ethylene using the catalyst.

16 Claims, 2 Drawing Sheets

[Example 1-Oligomerizing Catalyst I]

[Comparative Example 1-Comparative Catalyst A]

(51) Int. Cl.
*B01J 31/22* (2006.01)
*B01J 31/24* (2006.01)
*C07C 2/32* (2006.01)
*C07C 2/36* (2006.01)
*C08F 10/14* (2006.01)
*C08F 2/44* (2006.01)
*C08F 10/02* (2006.01)
*C08F 4/12* (2006.01)
*C08F 4/69* (2006.01)
*C07C 11/02* (2006.01)

(52) U.S. Cl.
CPC ............ *B01J 31/2495* (2013.01); *C07C 2/32* (2013.01); *C07C 2/36* (2013.01); *C08F 2/44* (2013.01); *C08F 4/12* (2013.01); *C08F 4/69* (2013.01); *C08F 10/02* (2013.01); *C08F 10/14* (2013.01); *B01J 2231/20* (2013.01); *B01J 2531/0205* (2013.01); *B01J 2531/62* (2013.01); *C07C 11/02* (2013.01)

(56) References Cited

U.S. PATENT DOCUMENTS

| | | | |
|---|---|---|---|
| 7,229,943 | B2 | 6/2007 | Gibson et al. |
| 7,285,607 | B2 | 10/2007 | Blann et al. |
| 7,425,661 | B2 | 9/2008 | McConville et al. |
| 7,511,183 | B2 | 3/2009 | Blann et al. |
| 8,609,924 | B2 | 12/2013 | Han et al. |
| 9,637,508 | B2 | 5/2017 | Lee et al. |
| 9,827,561 | B2 | 11/2017 | Sa et al. |
| 2010/0137669 | A1 | 6/2010 | Han et al. |
| 2016/0045906 | A1 | 2/2016 | Sa et al. |

FOREIGN PATENT DOCUMENTS

| | | |
|---|---|---|
| EP | 2107943 A1 | 10/2009 |
| EP | 2987783 A1 | 2/2016 |
| EP | 3118227 A1 | 1/2017 |
| JP | 8104692 A | 4/1996 |
| JP | 2016503815 A | 2/2016 |
| KR | 1020060002741 A | 1/2006 |
| KR | 1020080068226 A | 7/2008 |
| KR | 101065596 B1 | 9/2011 |
| KR | 1020150058018 A | 5/2015 |
| WO | 0204119 A1 | 1/2002 |
| WO | 2004056479 A1 | 7/2004 |
| WO | 2006096881 A1 | 9/2006 |

OTHER PUBLICATIONS

Angermun et al. Chemistry—A European Journal, 3(5), 755-764 (Year: 1997).*

Machine-generated English translation of Li et al. (CN 104086350 A).*

McAlees et al. (Organometallics, 1993, 12, 2445-2461). (Year: 1993).*

Fatila et al.; Syntheses and crystal structures of anhydrous Ln(hfac)3(monoglyme). Ln=La, Ce, Pr, Sm, Eu, Gd, Tb, Dy, Er, Tm†; Dalton Transactions; vol. 41, No. 4; Jan. 1, 2012; pp. 1352-1362.

Fornika et al.; Complexes [(P2)Rh(hfacac)] (P2 = Bidentate Chelating Phosphane, hfacac = Hexafluoroacetylacetonate) as Catalysts for CO2 Hydrogenation: Correlations between Solid State Structures, 103Rh NMR Shifts and Catalytic Activities†; Journal of the Chemical Society, Chemical Communications; No. 14, vol. 1; Jan. 1995 (Jan. 1, 1995); pp. 1479-1481.

Bollmann et al., "Ethylene Tetramerization: A New Route to Produce 1-Octene in Exceptionally High Selectivities", Journal of the American Chemical Society, 2004, pp. 14712-14713, vol. 126.

Carter et al., "High activity ethylene trimerisation catalysts based on diphosphine ligands", Chemical Communications, 2002, pp. 858-859, Issue 8.

Fei et al., "Influence of the functional group on the synthesis of aminophosphines, diphosphinoamines and iminobiphosphines", Dalton Transactions, 2003, pp. 2772-2779, Issue 13.

* cited by examiner

OLIGOMERIZATION CATALYST AND METHOD FOR PREPARING ETHYLENE OLIGOMER USING SAME

CROSS-REFERENCE TO RELATED APPLICATIONS

This application is the United States national phase of International Application No. PCT/KR2017/004849 filed May 11, 2017, and claims priority to Korean Patent Application No. 10-2016-0065709 filed May 27, 2016, the disclosures of which are hereby incorporated in their entirety by reference.

TECHNICAL FIELD

The present invention relates to a highly active and highly selective ethylene oligomerization catalyst for being used in an oligomerization reaction such as trimerization or tetramerization of ethylene, and a method for preparing 1-hexene or 1-octene using the same.

BACKGROUND ART

1-Hexene and 1-octene are important commercial raw materials widely used in polymerization processes as monomers or comonomers for preparing linear low density polyethylene, and are obtained by purifying a product produced by an oligomerization reaction of ethylene.

However, the conventional oligomerization reaction of ethylene has an ineffective aspect in that a significant amount of butene, high-grade oligomer, and polyethylene together with 1-hexene and 1-octene are produced together. This conventional oligomerization technique of ethylene generally prepares various α-olefins according to the Schulze-Flory or Poisson product distribution, and thus a desired product yield is limited.

Recently, studies have been conducted on preparation of 1-hexene by selective trimerization or on preparation of 1-octene by selective tetramerization through transition metal catalysis of ethylene, wherein most of the known transition metal catalysts are chromium-based catalysts. WO 02/04119 discloses a chromium-based catalyst using a ligand of General Formula $(R^1)(R^2)X$—Y—$X(R^3)(R^4)$ as an ethylene trimerization catalyst, wherein X is phosphorus, arsenic, or antimony, Y is a linking group such as —$N(R^5)$—, and at least one of $R^1$, $R^2$, $R^3$ and $R^4$ has a polar or electron donating substituent.

Another known document discloses the use of (o-ethylphenyl)$_2$PN(Me)P(o-ethylphenyl)$_2$ which is a compound that does not have a polar substituent in at least one of $R^1$, $R^2$, $R^3$ and $R^4$, as a ligand that does not exhibit catalytic activity with respect to 1-hexene under catalytic conditions (Antea Carter et al., Chem. Commun., 2002, p. 858-859).

In addition, it is known from Korean Patent Laid-Open Publication No. 2006-0002741 that it is practically possible to obtain excellent ethylene trimerization activity and selectivity by using a PNP ligand containing a non-polar substituent at the ortho position of a phenyl ring attached to phosphorus such as (o-ethylphenyl)$_2$PN(Me)P(o-ethylphenyl)$_2$.

Meanwhile, it is known from WO 04/056479 that a chromium-based catalyst containing a PNP ligand in which a substituent is omitted from a phenyl ring attached to phosphorus is capable of tetramerizing ethylene to improve selectivity in preparation of 1-octene, wherein (phenyl)$_2$PN (isopropyl)P(phenyl)$_2$, or the like, is described as an example of a heteroatom ligand used in the tetramerization catalyst for the ethylene tetramerization thereof.

This related art document discloses that the chromium-based catalyst containing a heteroatom ligand having nitrogen and phosphorus as heteroatoms is capable of tetramerizing ethylene even without a polar substituent with respect to the hydrocarbyl or heterohydrocarbyl group bonded to the phosphorus atom, such that 1-octene is prepared with selectivity over 70 mass %.

However, the related art documents fail to suggest a clear example of any specific form of a ligand structure including a heteroatom capable of tetramerizing ethylene in a highly selectively manner to prepare 1-octene or capable of trimerizing ethylene to prepare 1-hexene, merely suggest a PNP-type skeleton structure such as $(R^1)(R^2)P$—$(R^5)N$—P $(R^3)(R^4)$ as a ligand having about 70 mass % of 1-octene selectivity, and limitedly disclose types of substituents that are substitutable in the heteroatom ligand.

In addition, the PNP-type skeleton ligand including a heteroatom which is a related art technique has problems in that a reaction activity thereof is not consistently maintained and a reaction rate is greatly reduced according to the reaction time in reactions for preparing 1-octene or 1-hexene. Here, the nitrogen atoms included in the skeletal structure have a non-bonding electron pair to be easily coordinated with the transition metal, which is considered to be suitable as a ligand. However, the above problems are caused because phosphorus atoms having relatively weak coordination force lead to easy dissociation from the transition metal. The known document discloses that the PNP skeletal ligand is capable of being easily converted into the N=P—P structure from the P—N—P structure depending on synthetic environments, such as polarity of the solvent and substituent, and the like (Dalton Trans., 2003, 2772).

Meanwhile, it is known from another known document that when performing an ethylene oligomerization reaction by synthesizing the catalyst complex in advance with the ligand of the PNP type skeleton including a heteroatom and the chromium precursor, there is no significant change in activity and selectivity as compared to results obtained by separately injecting the ligand and the chromium precursor (J. Am. Chem. Soc., 2004, 126, 14712).

Meanwhile, since an activity increases when an aliphatic hydrocarbon compound is used as a solvent in the oligomerization reaction of ethylene using a chromium complex compound as a catalyst, it is advantageous in that the activity is better than a case where the aromatic compound is used as the polymerization solvent, and thus the use of the catalyst is capable of being significantly reduced. Nevertheless, most of the related art documents disclose preparation of 1-hexene or 1-octene by trimerizing or tetramerizing ethylene using an aromatic compound such as toluene, xylene, chlorobenzene, dichlorobenzene, or the like, as a polymerization solvent. This is because solubility of the chromium complex in an aliphatic hydrocarbon compound solvent is poor, and thus there is a problem in that it is not easy to control a catalyst amount when the catalyst solution is continuously introduced.

Therefore, it is urgent to develop an oligomerization catalyst having a structure in which solubility with respect to the aliphatic hydrocarbon compound that increases the ethylene oligomerization activity is high so that it is easy to control the catalyst amount, and ethylene is oligomerized in highly active and highly selective manner to be capable of preparing 1-hexene or 1-octene.

DISCLOSURE

Technical Problem

An object of the present invention is to provide a highly active and highly selective oligomerization catalyst having high solubility with respect to an aliphatic hydrocarbon compound for being used in an oligomerization reaction such as trimerization or tetramerization of ethylene, and a method for preparing an ethylene oligomer using the same.

Technical Solution

In one general aspect, an oligomerization catalyst includes a transition metal or transition metal precursor, a halogen-substituted organic ligand, and a heteroatom ligand.

In the oligomerization catalyst according to an embodiment of the present invention, the halogen-substituted organic ligand may be a monovalent anionic bidentate organic ligand, and may be a ligand that coordinates to a transition metal through a non-bonding electron pair of a carbon atom or a heteroatom selected from nitrogen, oxygen and sulfur.

The halogen-substituted organic ligand may be selected from the following structures, but is not limited thereto:

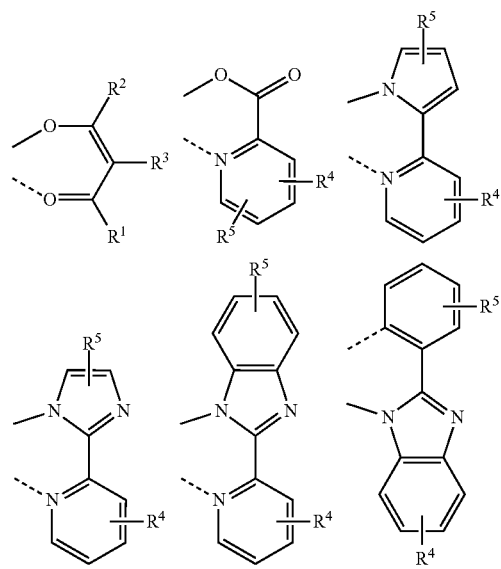

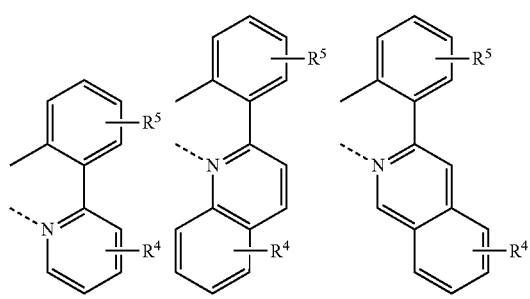

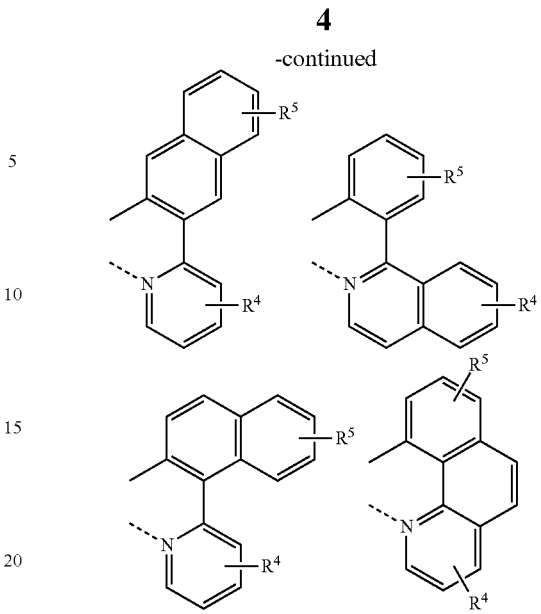

$R^1$ and $R^2$ are each independently halogen, hydrocarbyl, substituted hydrocarbyl, heterohydrocarbyl or substituted heterohydrocarbyl, $R^3$ is hydrogen, halogen, hydrocarbyl, substituted hydrocarbyl, heterohydrocarbyl or substituted heterohydrocarbyl, $R^1$ and $R^3$ or $R^2$ and $R^3$ may be linked by a hydrocarbylene, substituted hydrocarbylene, heterohydrocarbylene or substituted heterohydrocarbylene to form a ring, provided that at least one of $R^1$ to $R^3$ is halogen-substituted hydrocarbyl or halogen-substituted heterohydrocarbyl; and $R^4$ and $R^5$ are each independently hydrogen, hydrocarbyl, substituted hydrocarbyl, heterohydrocarbyl or substituted heterohydrocarbyl, provided that at least one of $R^4$ and $R^5$ is a halogen-substituted hydrocarbyl or halogen-substituted heterohydrocarbyl.

The halogen-substituted organic ligand may be a β-keto enolate type ligand, and may be more preferably an enolate-based ligand represented by Chemical Formula 1 below, but is not limited thereto:

[Chemical Formula 1]

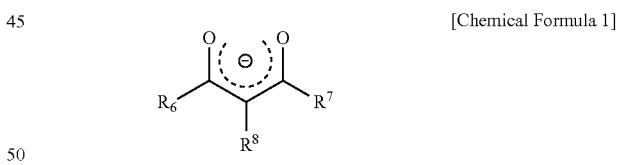

in Chemical Formula 1, $R^6$ and $R^7$ are each independently halogen, hydrocarbyl, substituted hydrocarbyl, heterohydrocarbyl or substituted heterohydrocarbyl;

$R^8$ is hydrogen, halogen, hydrocarbyl, substituted hydrocarbyl, heterohydrocarbyl, or substituted heterohydrocarbyl;

$R^6$ and $R^8$ or $R^7$ and $R^8$ may be linked by hydrocarbylene, substituted hydrocarbylene, heterohydrocarbylene or substituted heterohydrocarbylene to form a ring; and at least one of $R^6$ to $R^8$ is halogen-substituted hydrocarbyl or halogen-substituted heterohydrocarbyl.

At least one of $R^6$ to $R^8$ in Chemical Formula 1 above may be fluorine-substituted hydrocarbyl or fluorine-substituted heterohydrocarbyl.

The heteroatom ligand may be represented by General Formula $(R)_nA\text{-}B\text{---}C(R)_m$, wherein A and C are independently selected from the group consisting of phosphorus, arsenic, antimony, oxygen, bismuth, sulfur, selenium, and nitrogen, B is a linking group between A and C, R is the same as or different from each other and is each independently selected from the group consisting of hydrocarbyl, heterohydrocarbyl, substituted hydrocarbyl and substituted heterohydrocarbyl groups, and n and m are each determined as a valence and an oxidation state of A or C.

B may be selected from the group consisting of an organic linking group including hydrocarbyl, substituted hydrocarbyl, heterohydrocarbyl, and substituted heterohydrocarbyl; an inorganic linking group including a single atom link; an ion link; and methylene, dimethylmethylene, 1,2-ethylene, 1,2-phenylene, 1,2-propylene, 1,2-catechol, 2,3-butylene, 1,2-dimethyl hydrazine, —B(R')—, —Si(R')$_2$—, —P(R')—, and —N(R')—, and R' may be hydrogen, hydrocarbyl, substituted hydrocarbyl, heterohydrocarbyl, substituted heterohydrocarbyl, substituted heteroatom or halogen.

The heteroatom ligand may be specifically a ligand having a P—C—C—P skeleton structure represented by Chemical Formula 2 below, a ligand having a P—N—P skeleton structure represented by Chemical Formula 3 below, or a ligand having a P—C=C—P skeleton structure represented by Chemical Formula 4 below:

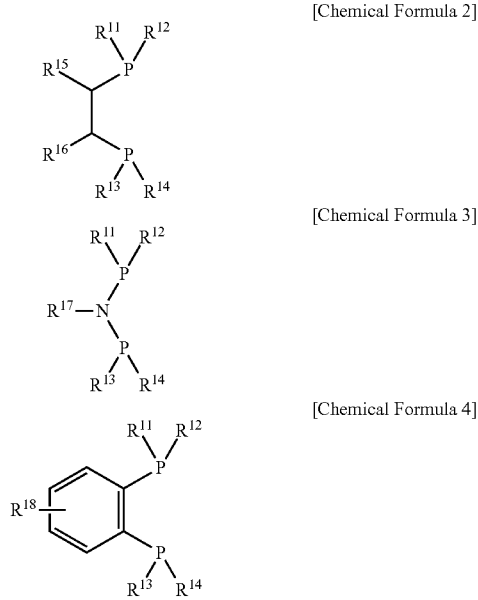

in Chemical Formulas 2 to 4, $R^{11}$ to $R^{14}$ are each independently hydrocarbyl, substituted hydrocarbyl, heterohydrocarbyl or substituted heterohydrocarbyl; and $R^{15}$ to $R^{18}$ are each independently hydrogen, hydrocarbyl, substituted hydrocarbyl, heterohydrocarbyl, substituted heterohydrocarbyl, or substituted heteroatom, or $R^{15}$ and $R^{16}$ may be bonded to each other by hydrocarbylene, substituted hydrocarbylene, heterohydrocarbylene, or substituted heterohydrocarbylene to form a ring.

The oligomerization catalyst may be mononuclear or binuclear.

The transition metal or transition metal precursor is not specifically limited, but may be a Group 4, Group 5 or Group 6 transition metal, or a precursor thereof.

The transition metal or transition metal precursor may be chromium, molybdenum, tungsten, titanium, tantalum, vanadium, zirconium or a precursor thereof.

The transition metal or transition metal precursor may be a chromium or chromium precursor.

The transition metal precursor may be selected from the group consisting of chromium (III) acetylacetonate, chromium (III) chloride tris-tetrahydrofuran, and chromium (III) 2-ethylhexanoate.

The oligomerization catalyst may be a complex in which a chromium or chromium precursor coordinates with an enolate-based ligand represented by Chemical Formula 1 below, and a ligand having a P—C—C—P skeleton structure represented by Chemical Formula 2 below, a ligand having a P—N—P skeleton structure represented by Chemical Formula 3 below, or a ligand having a P—C=C—P skeleton structure represented by Chemical Formula 4 below:

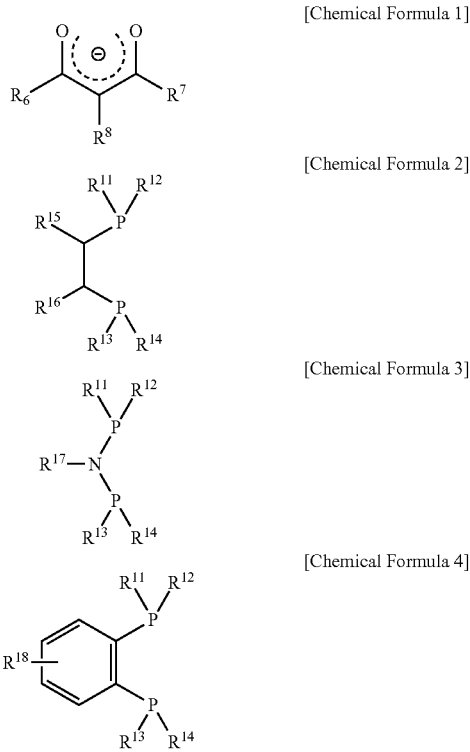

in Chemical Formulas 1 to 4, $R^6$ and $R^7$ are each independently fluorine-substituted (C1-C10)alkyl or fluorine-substituted (C6-C20)aryl, the fluorine-substituted alkyl and the fluorine-substituted aryl of $R^6$ and $R^7$ may be further substituted with one or more substituents selected from chloro, bromo, iodo, (C1-C10) alkyl, (C6-C20)aryl, halo(C1-C10)alkyl, and halo(C6-C20) aryl in addition to fluorine;

$R^8$ is hydrogen, halogen, (C1-C10)alkyl or (C6-C20)aryl; the alkyl and aryl of $R^8$ may be further substituted with one or more of halogen, (C1-C10)alkyl, (C6-C20)aryl, halo(C1-C10)alkyl, and halo(C6-C20)aryl;

$R^6$ and $R^8$ or $R^7$ and $R^8$ may be linked by (C3-C10) alkylene, (C3-C10)alkenylene, (C6-C20)arylene, (C3-C10) heteroalkylene, (C3-C10)heteroalkenylene or (C6-C20)heteroarylene to form a ring;

$R^{11}$ to $R^{14}$ are each independently (C6-C20)aryl, (C6-C20)ar(C1-C10)alkyl, (C1-C10)alkyl, (C2-C10)alkenyl, (C2-C10)alkynyl, (C1-C10)alkoxy, (C6-C20)aryloxy, (C3-C7)cycloalkyl, thio(C1-C10)alkyl, (C1-C10)alkylsilyl, (C6-C20)arylsilyl, (C3-C20)heteroaryl, 5- to 7-membered heterocycloalkyl or —$NR^{21}R^{22}$, the $R^{21}$ and $R^{22}$ are each independently (C1-C10)alkyl, (C6-C20)aryl or di(C1-C10)alkylamino;

$R^{15}$ to $R^{18}$ are each independently (C6-C20)aryl, (C6-C20)ar(C1-C10)alkyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, mono or di(C1-C10)alkylamino, (C1-C10)alkylsilyl or (C6-C20)arylsilyl, or $R^{15}$ and $R^{16}$ may be linked by (C3-C10)alkylene, (C3-C10)alkenylene, (C6-C20)arylene, (C3-C10)heteroalkylene, (C3-C10)heteroalkenylene or (C6-C20)heteroarylene to form a ring; and the aryl, aralkyl, alkyl, alkenyl, alkoxy, aryloxy, cycloalkyl, heteroaryl, heterocycloalkyl of $R^{11}$ to $R^{14}$, and the aryl, aralkyl, alkyl, alkenyl, cycloalkyl, heteroaryl, heterocycloalkyl, alkoxy, aryloxy, mono or dialkylamino, alkylsilyl or arylsilyl of $R^{15}$ to $R^{18}$ may be further substituted with one or more selected from the group consisting of (C1-C10)alkyl, (C2-C10)alkenyl, (C2-C10)alkynyl, (C1-C10)alkoxy, (C6-C20)aryloxy, (C1-C10)alkoxysilyl, 5- to 7-membered heterocycloalkyl, di(C1-C10)alkylamino, di(C2-C10)alkenylamino, di(C2-C10)alkynylamino, and halogen.

In another general aspect, there is provided a method for preparing an ethylene oligomer using an oligomerization catalyst composition including the oligomerization catalyst as described above and a cocatalyst.

The cocatalyst may be an organoaluminum compound, an organoboron compound, an organic salt, or a mixture thereof, but is not limited thereto.

The organoaluminum compound may include an aluminoxane-based compound, a compound of $AlR_3$ (wherein R is each independently (C1-C12)alkyl, (C6-C10)aryl, (C2-C10)alkenyl, (C2-C10)alkynyl, (C1-C12)alkoxy or halogen), or $LiAlH_4$, or the like, and the cocatalyst may be specifically methyl aluminoxane (MAO), modified methyl aluminoxane (MAO), ethyl aluminoxane (EAO), tetraisobutyl aluminoxane (TIBAO), isobutyl aluminoxane (IBAO), trimethyl aluminum (TMA), triethyl aluminum (TEA), triisobutyl aluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, or methylaluminum sesquichloride, but is not limited thereto.

An aliphatic hydrocarbon may be used as a reaction solvent.

The aliphatic hydrocarbon may be at least one selected from hexane, heptane, octane, nonane, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but is not limited thereto.

The ethylene oligomer may include 1-octene in an amount of 30 wt % or more.

The ethylene oligomer may include 1-octene in an amount of 50 wt % or more.

Advantageous Effects

Since the oligomerization catalyst according to the present invention further includes the halogen-substituted organic ligand in addition to the heteroatom ligand, when the oligomerization is performed using an aliphatic hydrocarbon compound as a polymerization solvent, the solubility of the catalyst may be higher than that of the conventionally used aromatic hydrocarbon compound, and thus the activity and the selectivity of the oligomerization reaction may be remarkably improved. In particular, the amount of the catalyst used may be reduced due to the high solubility of the catalyst with respect to the aliphatic hydrocarbon compound which increases the ethylene oligomerization activity, and the catalyst amount may be easily controlled when the catalyst solution is continuously supplied to the oligomerization reaction.

In addition, according to the present invention, the oligomer is prepared by using the oligomerization catalyst and simultaneously using the aliphatic hydrocarbon compound as the polymerization solvent instead of the conventionally used aromatic hydrocarbon compound. Thus, not only the operation stability and environmental pollution problem but also human toxicity problem caused by a small amount of residual solvent remaining in the product at the time of preparing the conventional oligomer, and the like, may be remarkably improved, and it is more economical since it is easy to recover the solvent after the polymerization.

BEST MODE

Figure 1:
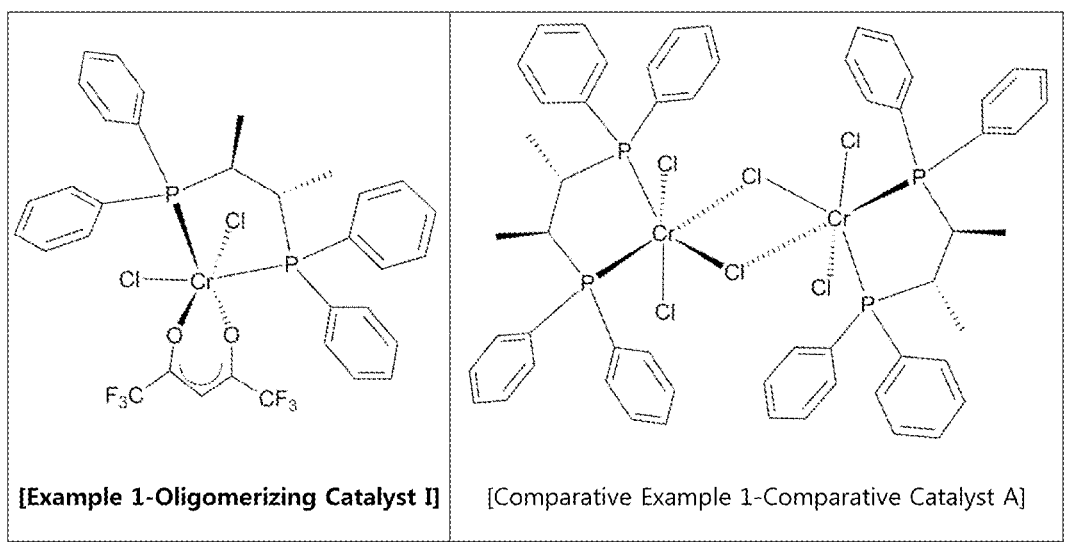
FIG. 1 shows structures of catalysts prepared in Example 1 and Comparative Example 1, respectively.

The present invention provides an oligomerization catalyst including a transition metal or transition metal precursor, a halogen-substituted organic ligand, and a heteroatom ligand.

The oligomerization catalyst of the present invention has a structure in which the halogen-substituted organic ligand is introduced into the catalyst, unlike the related arts, thereby being advantageous to have a high solubility with respect to an aliphatic hydrocarbon compound rather than an aromatic hydrocarbon compound due to the halogen-substituted organic ligand which is additionally introduced, and thus it is easy to control a catalyst amount in an oligomerization reaction of ethylene. In addition, the oligomerization catalyst including the halogen-substituted organic ligand may increase an activity when the aliphatic hydrocarbon compound rather than the aromatic hydrocarbon compound is used as a polymerization solvent, and thus the use of the catalyst may be largely reduced.

In the oligomerization catalyst according to an embodiment of the present invention, the halogen-substituted organic ligand may be a fluorine-substituted organic ligand.

In the oligomerization catalyst according to an embodiment of the present invention, the halogen-substituted organic ligand, which is a monovalent anionic bidentate organic ligand, may be a ligand that coordinates to a transition metal through a non-bonding electron pair of a carbon atom or a heteroatom selected from nitrogen, oxygen and sulfur.

Preferably, the halogen-substituted organic ligand may be selected from the following structures:

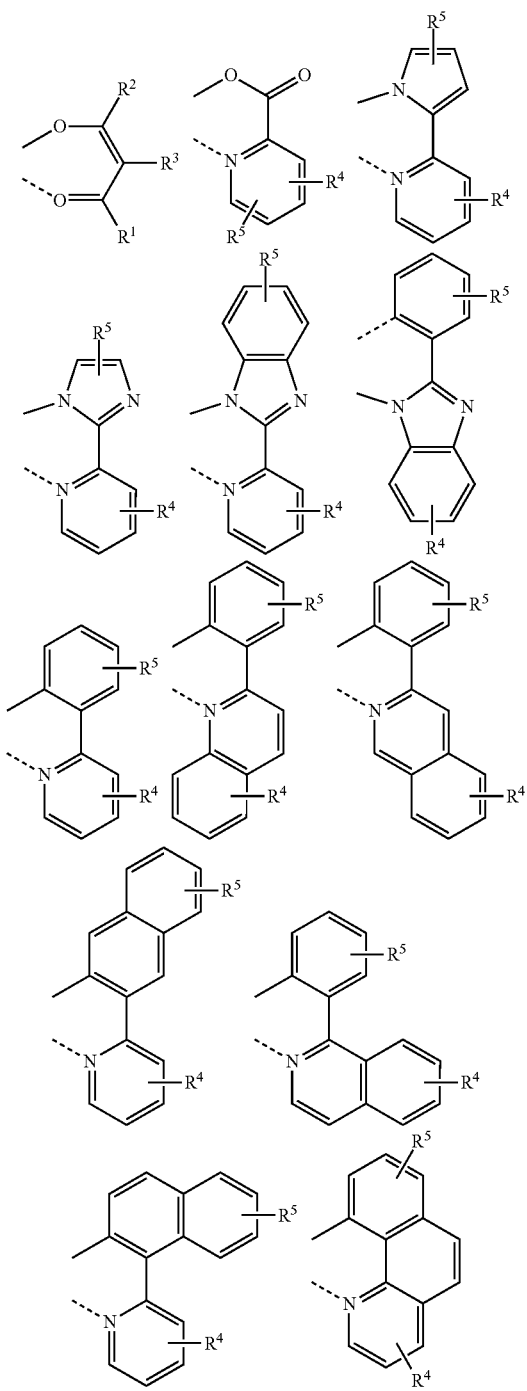

$R^1$ and $R^2$ are each independently halogen, hydrocarbyl, substituted hydrocarbyl, heterohydrocarbyl or substituted heterohydrocarbyl, $R^3$ is hydrogen, halogen, hydrocarbyl, substituted hydrocarbyl, heterohydrocarbyl or substituted heterohydrocarbyl, $R^1$ and $R^3$ or $R^2$ and $R^3$ may be linked by a hydrocarbylene, substituted hydrocarbylene, heterohydrocarbylene or substituted heterohydrocarbylene to form a ring, provided that at least one of $R^1$ to $R^3$ is halogen-substituted hydrocarbyl or halogen-substituted heterohydrocarbyl; and $R^4$ and $R^5$ are each independently hydrogen, hydrocarbyl, substituted hydrocarbyl, heterohydrocarbyl or substituted heterohydrocarbyl, provided that at least one of $R^4$ and $R^5$ is a halogen-substituted hydrocarbyl or halogen-substituted heterohydrocarbyl.

The "hydrocarbyl" or "heterohydrocarbyl" used herein means a radical having one bonding position derived from hydrocarbon or heterohydrocarbon, and the "hydrocarbylene" means a radical having two bonding positions derived from hydrocarbon, wherein the hetero means that the carbon is substituted with one or more heteroatoms selected from O, S, Se, Si, As, P, B and N atoms.

The "halogen-substituted" used herein means that at least one halogen is substituted.

The "substituted" used herein refers to a group or moiety having one or more substituents attached to a structural skeleton of the group or the moiety. The "substituted hydrocarbyl", "substituted heterohydrocarbyl", "substituted hydrocarbylene" or "substituted heterohydrocarbylene" means that the hydrocarbyl, heterohydrocarbyl, hydrocarbylene or heterohydrocarbylene is each independently further substituted with one or more substituents selected from the group consisting of (C1-C10)alkyl, (C2-C10)alkenyl, (C2-C10)alkynyl, (C1-C10)alkoxy, (C6-C20)aryl, (C6-C20)aryloxy, halo(C1-C10)alkyl, halo(C6-C20)aryl, (C1-C10)alkoxysilyl, 5- to 7-membered heterocycloalkyl, di(C1-C10)alkylamino, di(C2-C10)alkenylamino, di(C2-C10)alkynylamino, di(C6-C20)arylamino, and halogen.

The term "halo" or "halogen" of the present invention means fluorine, chlorine, bromine or iodine atom.

In addition, the term "aryl" used herein, which is an aromatic ring monovalent organic radical derived from an aromatic hydrocarbon by removal of one hydrogen, includes single or fused ring system including ring atoms of suitably 4 to 7, preferably, 5 or 6, in each ring, and also includes a form in which a plurality of aryls are connected by a single bond. Specific examples of aryl may include, but are not limited to, phenyl, naphthyl, biphenyl, anthryl, indenyl, fluorenyl, and the like.

The term "alkyl" used herein means a monovalent linear or branched saturated hydrocarbon radical composed of only carbon atoms and hydrogen atoms. Examples of the alkyl radical include, but are not limited to, methyl, ethyl, propyl, isopropyl, butyl, isobutyl, t-butyl, pentyl, hexyl, octyl, nonyl, and the like.

The term "alkenyl" used herein refers to a linear or branched unsaturated monovalent hydrocarbon radical including at least one double bond between two or more carbon atoms. Specific examples of the alkenyl may include, but are not limited to, ethynyl, propenyl, prop-1-en-2yl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like.

The term "alkynyl" used herein is a linear or branched unsaturated monovalent hydrocarbon radical including at least one triple bond between two or more carbon atoms. Specific examples of the alkynyl may include, but are not limited to, ethynyl, propynyl, 1-butynyl, 2-butynyl, 1-pentynyl, 2-pentynyl, 3-methyl-1-butynyl, and the like.

The term "alkoxy" used herein means an —O-alkyl radical, wherein the "alkyl" is the same as defined above. Examples of the alkoxy radical may include, but are not limited to, methoxy, ethoxy, isopropoxy, butoxy, isobutoxy, t-butoxy, and the like.

The term "aryloxy" used herein means an —O-aryl radical, wherein the "aryl" is the same as defined above. Examples of the aryloxy radical may include, but are not limited to, phenoxy, naphthoxy, and the like.

The term "alkoxycarbonyl" used herein means a C(=O) alkoxy radical, wherein the "alkoxy" is the same as defined above. Examples of the alkoxycarbonyl radical may include, but are not limited to, methoxycarbonyl, ethoxycarbonyl, isopropoxycarbonyl, propoxycarbonyl, butoxycarbonyl, isobutoxycarbonyl, t-butoxycarbonyl, and the like.

The term "alkylcarbonyloxy" used herein means an —OC(=O)alkyl radical, wherein the "alkyl" is the same as defined above. Examples of the alkylcarbonyloxy radical may include, but are not limited to, methylcarbonyloxy, ethylcarbonyloxy, isopropylcarbonyloxy, propylcarbonyloxy, butylcarbonyloxy, isobutylcarbonyloxy, t-butylcarbonyloxy, and the like.

The term "alkenylcarbonyloxy" used herein means an —OC(=O)alkenyl radical, wherein the "alkenyl" is the same as defined above. Examples of the alkenylcarbonyloxy radical may include, but are not limited to, ethenylcarbonyloxy, butenylcarbonyloxy, and the like.

The term "alkynylcarbonyloxy" used herein means an —OC(=O)alkynyl radical, wherein the "alkynyl" is the same as defined above. Examples of the alkynylcarbonyloxy radical may include, but are not limited to, ethynylcarbonyloxy, butynylcarbonyloxy, and the like.

The term "cycloalkyl" used herein means a monovalent saturated carbocyclic radical composed of one or more rings. Examples of cycloalkyl radical may include, but are not limited to, cyclopropyl, cyclobutyl, cyclopentyl, cyclohexyl, cycloheptyl, and the like.

Term "heteroaryl" used herein, which means a heteroaromatic ring monovalent radical which is an aryl group including 1 to 4 heteroatoms selected from N, O, and S as an aromatic ring skeleton atom and carbon as the remaining aromatic ring skeleton atom, is a 5- to 6-membered monocyclic heteroaryl and a polycyclic heteroaryl condensed with at least one benzene ring, and may be partially saturated. In addition, the heteroaryl in the present invention includes even a form in which one or more heteroaryls are connected by a single bond. Examples of the heteroaryl group may include, but are not limited to, pyrrolyl, pyrazolyl, quinolyl, isoquinolyl, pyridyl, pyrimidinyl, oxazolyl, triazolyl, thiadiazolyl, triazolyl, imidazolyl, benzoimidazolyl, isooxazolyl, benzoisooxazolyl, thiophenyl, benzothiophenyl, furyl, benzofuryl, and the like.

The term "heterocycloalkyl" used herein is a monovalent radical of a 5- to 7-membered non-aromatic hetero ring including 1 to 4 heteroatoms selected from N, O and S, wherein the non-aromatic hetero ring may have a saturated or unsaturated single ring form, and may be bonded via a heteroatom or a carbon atom. Examples of the heterocycloalkyl radical may include monovalent radicals of non-aromatic hetero rings such as pyrrolidine, piperidine, tetrahydropyridine, piperazine, morpholine, thiomorpholine, and the like.

In addition, the alkyl, alkoxy, alkenyl or alkynyl radical used herein may be limited to have 1 to 10 carbon atoms or 1 to 7 carbon atoms. The aryl radical may be limited to have 6 to 20 carbon atoms, or 6 to 12 carbon atoms. The heteroaryl radical may be limited to have 3 to 20 carbon atoms, or 4 to 12 carbon atoms.

The halogen-substituted organic ligand is more preferably a β-Keto enolate type ligand, and more preferably be an enolate-based ligand represented by Chemical Formula 1 below:

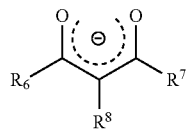

[Chemical Formula 1]

in Chemical Formula 1, $R^6$ and $R^7$ are each independently halogen, hydrocarbyl, substituted hydrocarbyl, heterohydrocarbyl or substituted heterohydrocarbyl;

$R^8$ is hydrogen, halogen, hydrocarbyl, substituted hydrocarbyl, heterohydrocarbyl, or substituted heterohydrocarbyl;

$R^6$ and $R^8$ or $R^7$ and $R^8$ may be linked by hydrocarbylene, substituted hydrocarbylene, heterohydrocarbylene or substituted heterohydrocarbylene to form a ring; and at least one of $R^6$ to $R^8$ is halogen-substituted hydrocarbyl or halogen-substituted heterohydrocarbyl.

In the oligomerization catalyst according to an embodiment of the present invention, at least one of $R^6$ to $R^8$ in Chemical Formula 1 above may be preferably fluorine-substituted hydrocarbyl or fluorine-substituted heterohydrocarbyl.

In Chemical Formula 1 above, $R^6$ and $R^7$ are each independently halogen, (C6-C20)aryl, halogen-substituted (C6-C20)aryl, (C6-C20)ar(C1-C10)alkyl, halogen-substituted (C6-C20)ar(C1-C10)alkyl, (C1-C10)alkyl, halogen-substituted (C1-C10)alkyl, (C6-C20)ar(C2-C10)alkenyl, halogen-substituted (C6-C20)ar(C2-C10)alkenyl, (C2-C10)alkenyl, halogen-substituted (C2-C10)alkenyl, (C6-C20)ar(C2-C10)alkynyl, halogen-substituted (C6-C20)ar(C2-C10)alkynyl, (C2-C10)alkynyl, halogen-substituted (C2-C10)alkynyl, (C1-C10)alkoxy, halogen-substituted (C1-C10)alkoxy, (C6-C20)aryloxy, halogen-substituted (C6-C20)aryloxy, (C1-C10)alkoxycarbonyl, halogen-substituted (C1-C10)alkoxycarbonyl, (C1-C10)alkylcarbonyloxy, halogen-substituted (C1-C10)alkylcarbonyloxy, (C2-C10)alkenylcarbonyloxy, halogen-substituted (C2-C10)alkenylcarbonyloxy, (C2-C10)alkynylcarbonyloxy, halogen-substituted (C2-C10)alkynylcarbonyloxy, (C3-C7)cycloalkyl, halogen-substituted (C3-C7)cycloalkyl, (C1-C10)alkylsilyl, halogen-substituted (C1-C10)alkylsilyl, (C2-C10)alkenylsilyl, halogen-substituted (C2-C10)alkenylsilyl, (C2-C10)alkynylsilyl, halogen-substituted (C2-C10)alkynylsilyl, (C6-C20)arylsilyl, halogen-substituted (C6-C20)arylsilyl, (C3-C20)heteroaryl, halogen-substituted (C3-C20)heteroaryl, 5- to 7-membered heterocycloalkyl or halogen-substituted 5- to 7-membered heterocycloalkyl;

$R^8$ may be further substituted with one or more selected from hydrogen, halogen, (C6-C20)aryl, halogen-substituted (C6-C20)aryl, (C6-C20)ar(C1-C10)alkyl, halogen-substituted (C6-C20)ar(C1-C10)alkyl, (C1-C10)alkyl, halogen-substituted (C1-C10)alkyl, (C6-C20)ar(C2-C10)alkenyl, halogen-substituted (C6-C20)ar(C2-C10)alkenyl, (C2-C10)alkenyl, halogen-substituted (C2-C10)alkenyl, (C6-C20)ar(C2-C10)alkynyl, halogen-substituted (C6-C20)ar(C2-C10)alkynyl, (C2-C10)alkynyl, halogen-substituted (C2-C10)alkynyl, (C1-C10)alkoxy, halogen-substituted (C1-C10)alkoxy, (C6-C20)aryloxy, halogen-substituted (C6-C20)aryloxy, (C1-C10)alkoxycarbonyl, halogen-substituted (C1-C10)alkoxycarbonyl, (C1-C10)alkylcarbonyloxy, halogen-substituted (C1-C10)alkylcarbonyloxy, (C2-C10)alkenylcarbonyloxy, halogen-substituted (C2-C10)alkenylcarbonyloxy, (C2-C10)alkynylcarbonyloxy, halogen-substituted (C2-C10)alkynylcarbonyloxy, (C3-C7)

cycloalkyl, halogen-substituted (C3-C7)cycloalkyl, (C1-C10)alkylsilyl, halogen-substituted (C1-C10)alkylsilyl, (C2-C10)alkenylsilyl, halogen-substituted (C2-C10)alkenylsilyl, (C2-C10)alkynylsilyl, halogen-substituted (C2-C10)alkynylsilyl, (C6-C20)arylsilyl, halogen-substituted (C6-C20)arylsilyl, (C3-C20)heteroaryl, halogen-substituted (C3-C20)heteroaryl, 5- to 7-membered heterocycloalkyl or halogen-substituted 5- to 7-membered heterocycloalkyl; and the aryl, aralkyl, alkyl, aralkenyl, alkenyl, aralkynyl, alkynyl, alkoxy, aryloxy, cycloalkyl, heteroaryl and heterocycloalkyl of $R^6$, $R^7$ and $R^8$ may be further substituted with one or more selected from (C1-C10)alkyl, (C2-C10)alkenyl, (C2-C10)alkynyl, (C1-C10)alkoxy, (C6-C20)aryl, (C6-C20)aryloxy, halo(C1-C10)alkyl, halo(C6-C20)aryl and halogen;

$R^6$ and $R^8$ or $R^7$ and $R^8$ may be linked by (C3-C10)alkylene, (C3-C10)alkenylene, (C6-C20)arylene, (C3-C10)heteroalkylene, (C3-C10)heteroalkenylene or (C6-C20)heteroarylene to form a ring;

at least one of $R^6$ to $R^8$ is halogen-substituted (C6-C20)aryl, halogen-substituted (C6-C20)ar(C1-C10)alkyl, halogen-substituted (C1-C10)alkyl, halogen-substituted (C6-C20)ar(C2-C10)alkenyl, halogen-substituted (C2-C10)alkenyl, halogen-substituted (C6-C20)ar(C2-C10)alkynyl, halogen-substituted (C2-C10)alkynyl, halogen-substituted (C1-C10)alkoxy, halogen-substituted (C6-C20)aryloxy, halogen-substituted (C1-C10)alkoxycarbonyl, halogen-substituted (C1-C10)alkylcarbonyloxy, halogen-substituted (C2-C10)alkenylcarbonyloxy, halogen-substituted (C2-C10)alkynylcarbonyloxy, halogen-substituted (C3-C7)cycloalkyl, halogen-substituted (C1-C10)alkylsilyl, halogen-substituted (C2-C10)alkenylsilyl, halogen-substituted (C2-C10)alkynylsilyl, halogen-substituted (C6-C20)arylsilyl, halogen-substituted (C3-C20)heteroaryl or halogen-substituted 5- to 7-membered heterocycloalkyl.

In Chemical Formula 1, preferably, $R^6$ and $R^7$ are each halogen, (C6-C20)aryl, halogen-substituted (C6-C20)aryl, (C6-C20)ar(C1-C10)alkyl, halogen-substituted (C6-C20)ar(C1-C10)alkyl, (C1-C10)alkyl, halogen-substituted (C1-C10)alkyl, (C6-C20)ar(C2-C10)alkenyl, halogen-substituted (C6-C20)ar(C2-C10)alkenyl, (C2-C10)alkenyl, halogen-substituted (C2-C10)alkenyl, (C6-C20)ar(C2-C10)alkynyl, halogen-substituted (C6-C20)ar(C2-C10)alkynyl, (C2-C10)alkynyl, halogen-substituted (C2-C10)alkynyl, (C1-C10)alkoxy, halogen-substituted (C1-C10)alkoxy, (C6-C20)aryloxy, halogen-substituted (C6-C20)aryloxy, (C1-C10)alkylcarbonyloxy, halogen-substituted (C1-C10)alkylcarbonyloxy, (C2-C10)alkenylcarbonyloxy, halogen-substituted (C2-C10)alkenylcarbonyloxy, (C2-C10)alkynylcarbonyloxy, halogen-substituted (C2-C10)alkynylcarbonyloxy, (C3-C7)cycloalkyl, halogen-substituted (C3-C7)cycloalkyl, (C1-C10)alkylsilyl, halogen-substituted (C1-C10)alkylsilyl, (C2-C10)alkenylsilyl, halogen-substituted (C2-C10)alkenylsilyl, (C2-C10)alkynylsilyl, halogen-substituted (C2-C10)alkynylsilyl, (C6-C20)arylsilyl, halogen-substituted (C6-C20)arylsilyl, (C3-C20)heteroaryl, halogen-substituted (C3-C20)heteroaryl, 5- to 7-membered heterocycloalkyl or halogen-substituted 5- to 7-membered heterocycloalkyl, and at least one of $R^6$ and $R^7$ is halogen-substituted (C6-C20)aryl, halogen-substituted (C6-C20)ar(C1-C10)alkyl, halogen-substituted (C1-C10)alkyl, halogen-substituted (C6-C20)ar(C2-C10)alkenyl, halogen-substituted (C2-C10)alkenyl, halogen-substituted (C6-C20)ar(C2-C10)alkynyl, halogen-substituted (C2-C10)alkynyl, halogen-substituted (C1-C10)alkoxy, halogen-substituted (C6-C20)aryloxy, halogen-substituted (C1-C10)alkylcarbonyloxy, halogen-substituted (C2-C10)alkenylcarbonyloxy, halogen-substituted (C2-C10)alkynylcarbonyloxy, halogen-substituted (C3-C7)cycloalkyl, halogen-substituted (C1-C10)alkylsilyl, halogen-substituted (C2-C10)alkenylsilyl, halogen-substituted (C2-C10)alkynylsilyl, halogen-substituted (C6-C20)arylsilyl, halogen-substituted (C3-C20)heteroaryl or halogen-substituted 5- to 7-membered heterocycloalkyl; $R^8$ is hydrogen, halogen, (C6-C20)aryl, (C1-C10)alkyl, (C2-C10)alkenyl, (C2-C10)alkynyl, (C1-C10)alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, (C3-C7)cycloalkyl, (C1-C10)alkylsilyl, (C6-C20)arylsilyl, (C2-C10)alkenylsilyl, (C2-C10)alkynylsilyl, (C3-C20)heteroaryl or 5- to 7-membered heterocycloalkyl;

$R^6$ and $R^8$ or $R^7$ and $R^8$ may be linked by (C3-C10)alkylene, (C3-C10)alkenylene, (C6-C20)arylene, (C3-C10)heteroalkylene, (C3-C10)heteroalkenylene or (C6-C20)heteroarylene to form a ring;

The aryl, aralkyl, alkyl, aralkenyl, alkenyl, aralkynyl, alkynyl, alkoxy, aryloxy, cycloalkyl, heteroaryl, and heterocycloalkyl of $R^6$, $R^7$ and $R^8$ may be further substituted with one or more selected from (C1-C10)alkyl, (C2-C10)alkenyl, (C2-C10)alkynyl, (C1-C10)alkoxy, (C6-C20)aryl, (C6-C20)aryloxy, halo(C1-C10)alkyl, halo(C6-C20)aryl and halogen.

More preferably, $R^6$ and $R^7$ of Chemical Formula 1 are each independently fluorine-substituted (C6-C20)aryl, fluorine-substituted (C6-C20)ar(C1-C10)alkyl, fluorine-substituted (C1-C10)alkyl, fluorine-substituted (C6-C20)ar(C2-C10)alkenyl, fluorine-substituted (C2-C10)alkenyl, fluorine-substituted (C6-C20)ar(C2-C10)alkynyl, fluorine-substituted (C2-C10)alkynyl, fluorine-substituted (C1-C10)alkoxy, fluorine-substituted (C6-C20)aryloxy, fluorine-substituted (C1-C10)alkylcarbonyloxy, fluorine-substituted (C2-C10)alkenylcarbonyloxy, fluorine-substituted (C2-C10)alkynylcarbonyloxy, fluorine-substituted (C3-C7)cycloalkyl, fluorine-substituted (C1-C10)alkylsilyl, fluorine-substituted (C2-C10)alkenylsilyl, fluorine-substituted (C2-C10)alkynylsilyl, fluorine-substituted (C6-C20)arylsilyl, fluorine-substituted (C3-C20)heteroaryl or fluorine-substituted 5- to 7-membered heterocycloalkyl; $R^8$ is hydrogen, halogen, (C6-C20)aryl, (C1-C10)alkyl, (C2-C10)alkenyl, (C2-C10)alkynyl, (C1-C10)alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, (C3-C7)cycloalkyl, (C1-C10)alkylsilyl, (C2-C10)alkenylsilyl, (C2-C10)alkynylsilyl, (C6-C20)arylsilyl, (C3-C20)heteroaryl or 5- to 7-membered heterocycloalkyl;

$R^6$ and $R^8$ or $R^7$ and $R^8$ may be linked by (C3-C10)alkylene, (C3-C10)alkenylene, (C6-C20)arylene, (C3-C10)heteroalkylene, (C3-C10)heteroalkenylene or (C6-C20)heteroarylene to form a ring; and the aryl, aralkyl, alkyl, aralkenyl, alkenyl, aralkynyl, alkynyl, alkoxy, aryloxy, cycloalkyl, heteroaryl, and heterocycloalkyl of $R^6$, $R^7$ and $R^8$ may be further substituted with one or more selected from (C1-C10)alkyl, (C2-C10)alkenyl, (C2-C10)alkynyl, (C1-C10)alkoxy, (C6-C20)aryl, (C6-C20)aryloxy, halo(C1-C10)alkyl, halo(C6-C20)aryl and halogen.

More preferably, in Chemical Formula 1, $R^6$ and $R^7$ are each independently fluorine-substituted (C1-C10)alkyl or fluorine-substituted (C6-C20)aryl, and the fluorine-substituted alkyl and fluorine-substituted aryl of $R^6$ and $R^7$ may be further substituted with one or more substituents selected from chloro, bromo, (C1-C10)alkyl, (C6-C20)aryl, halo(C1-C10)alkyl and halo(C6-C20)aryl in addition to fluorine; $R^8$ is hydrogen, halogen, (C1-C10)alkyl or (C6-C20)aryl, and the alkyl and aryl of $R^8$ may be further substituted with one or more selected from halogen, (C1-C10)alkyl, (C6-C20)aryl, halo(C1-C10)alkyl, and halo(C6-C20)aryl.

The enolate-based ligand represented by Chemical Formula 1 may be exemplified by the following structures, but is not limited thereto:

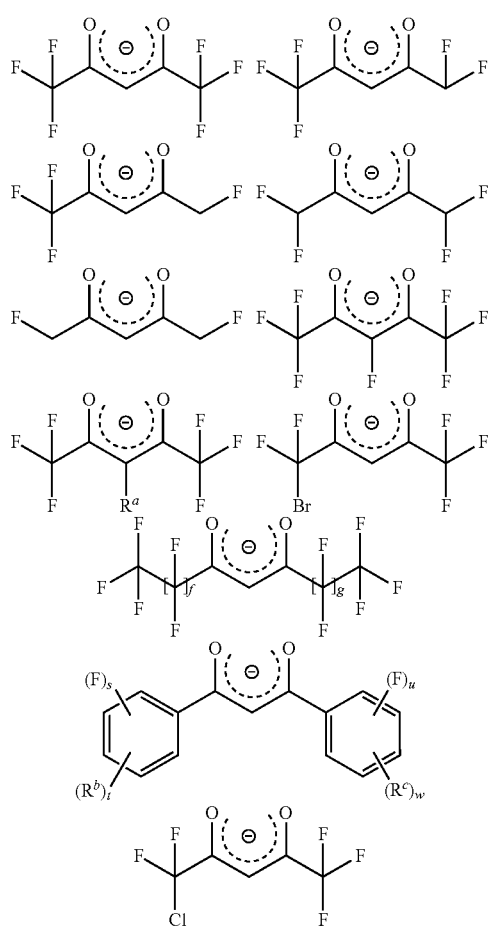

$R^a$ is (C1-C10)alkyl or (C6-C20)aryl, the alkyl and aryl of $R^a$ may be further substituted with one or more selected from halogen, (C1-C10)alkyl, (C6-C20)aryl, halo(C1-C10)alkyl and halo(C6-C20)aryl; $R^b$ and $R^c$ are each independently chloro, bromo, (C1-C10)alkyl, (C6-C20)aryl, halo(C1-C10) alkyl, and halo (C6-C20)aryl; f is an integer of 0 to 9; g is an integer of 1 to 9; s and u are each independently an integer of 1 to 5; t and w are each independently an integer of 0 to 4, provided that the sum of s and t and the sum of u and w is 5.

Even more preferably, $R^6$ and $R^7$ in Chemical Formula 1 are each independently fluorine-substituted (C1-C10)alkyl; and $R^8$ is hydrogen, fluoro or (C1-C10)alkyl.

The heteroatom ligand may be represented by General Formula $(R)_nA-B-C(R)_m$, wherein A and C are independently selected from the group consisting of phosphorus, arsenic, antimony, oxygen, bismuth, sulfur, selenium, and nitrogen, B is a linking group between A and C, R is the same as or different from each other and is each independently selected from the group consisting of hydrocarbyl, heterohydrocarbyl, substituted hydrocarbyl and substituted heterohydrocarbyl groups, and n and m are each determined as a valence and an oxidation state of A or C.

In the heteroatom ligand represented by General Formula $(R)_nA-B-C(R)_m$, B may be selected from the group consisting of an organic linking group including hydrocarbyl, substituted hydrocarbyl, heterohydrocarbyl, and substituted heterohydrocarbyl; an inorganic linking group including a single atom link; an ion link; and methylene, dimethylmethylene, 1,2-ethylene, 1,2-phenylene, 1,2-propylene, 1,2-catechol, 2,3-butylene, 1,2-dimethyl hydrazine, —B(R')—, —Si(R')$_2$—, —P(R')—, and —N(R')—, and R' may be hydrogen, hydrocarbyl, substituted hydrocarbyl, heterohydrocarbyl, substituted heterohydrocarbyl, substituted heteroatom or halogen.

The heteroatom ligand may be a ligand having a P—C—C—P skeleton structure represented by Chemical Formula 2 below, a ligand having a P—N—P skeleton structure represented by Chemical Formula 3 below, or a ligand having a P—C=C—P skeleton structure represented by Chemical Formula 4 below:

[Chemical Formula 2]

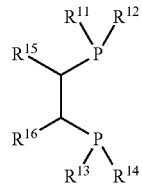

[Chemical Formula 3]

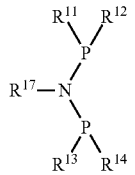

[Chemical Formula 4]

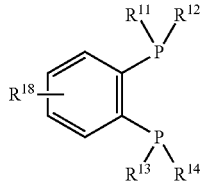

in Chemical Formulas 2 to 4, $R^{11}$ to $R^{14}$ are each independently hydrocarbyl, substituted hydrocarbyl, heterohydrocarbyl or substituted heterohydrocarbyl; and $R^{15}$ to $R^{18}$ are each independently hydrogen, hydrocarbyl, substituted hydrocarbyl, heterohydrocarbyl, substituted heterohydrocarbyl, or substituted heteroatom, or $R^{15}$ and $R^{16}$ may be bonded to each other by hydrocarbylene, substituted hydrocarbylene, heterohydrocarbylene, or substituted heterohydrocarbylene to form a ring.

$R^{11}$ to $R^{14}$ in Chemical Formulas 2 to 4 are each independently (C6-C20)aryl, (C6-C20)ar(C1-C10)alkyl, (C6-C20)ar(C2-C10)alkenyl, (C6-C20)ar(C2-C10)alkynyl, (C1-C10)alkyl, (C2-C10)alkenyl, (C2-C10)alkynyl, (C1-C10) alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, aminocarbonyl, (C1-C10) alkylcarbonylamino, (C2-C10)alkenylcarbonylamino, (C2-C10)alkynylcarbonylamino, (C3-C7)cycloalkyl, thio(C1-C10)alkyl, thio(C2-C10)alkenyl, thio(C2-C10)alkynyl, (C1-C10)alkylsilyl, (C2-C10)alkenylsilyl, (C2-C10)alkynylsilyl, (C6-C20)arylsilyl, (C3-C20)heteroaryl, 5- to 7-membered heterocycloalkyl or —NR$^{21}$R$^{22}$, the R$^{21}$ and R$^{22}$ are each independently (C1-C10)alkyl, (C2-C10)alkenyl, (C2-C10)

alkynyl, (C6-C20)aryl, di(C1-C10)alkylamino, di(C2-C10)alkenylamino or di(C2-C10)alkynylamino;

$R^{15}$ to $R^{18}$ are each independently (C6-C20)aryl, (C6-C20)ar(C1-C10)alkyl, (C6-C20)ar(C2-C10)alkenyl, (C6-C20)ar(C2-C10)alkynyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, (C1-C10)alkoxycarbonyl, (C1-C10)alkylcarbonyloxy, (C2-C10)alkenylcarbonyloxy, (C2-C10)alkynylcarbonyloxy, aminocarbonyl, (C1-C10)alkylcarbonylamino, (C2-C10)alkenylcarbonylamino, (C2-C10)alkynylcarbonylamino, di(C1-C10)alkylamino, di(C2-C10)alkenylamino, di(C2-C10)alkynylamino, (C1-C10)alkylsilyl, (C2-C10)alkenylsilyl, (C2-C10)alkynylsilyl or (C6-C20)arylsilyl, or the $R^{15}$ and $R^{16}$ may be linked by (C3-C10)alkylene or (C3-C10)alkenylene to form a ring; and the aryl, aralkyl, aralkenyl, aralkynyl, alkyl, alkenyl, alkoxy, aryloxy, alkoxycarbonyl, alkylcarbonyloxy, alkenylcarbonyloxy, alkynylcarbonyloxy, cycloalkyl, heteroaryl, heterocycloalkyl of $R^{11}$ to $R^{14}$, and the aryl, aralkyl, aralkenyl, aralkynyl, alkyl, alkenyl, cycloalkyl, heteroaryl, heterocycloalkyl, alkoxy, aryloxy, alkoxycarbonyl, alkylcarbonyloxy, alkenylcarbonyloxy, alkynylcarbonyloxy, aminocarbonyl, alkylcarbonylamino, alkenylcarbonylamino, alkynylcarbonylamino, dialkylamino, dialkenylamino, dialkynylamino, alkylsilyl, alkenylsilyl, alkynylsilyl, or arylsilyl of $R^{15}$ to $R^{18}$ may be further substituted with one or more selected from the group consisting of (C1-C10)alkyl, (C2-C10)alkenyl, (C2-C10)alkynyl, (C1-C10)alkoxy, (C6-C20)aryloxy, (C1-C10)alkoxysilyl, 5- to 7-membered heterocycloalkyl, di(C1-C10)alkylamino, di(C2-C10)alkenylamino, di(C2-C10)alkynylamino, and halogen.

In Chemical Formulas 2 to 4, more preferably, $R^{11}$ to $R^{14}$ are each independently (C6-C20)aryl, (C6-C20)ar(C1-C10)alkyl, (C1-C10)alkyl, (C2-C10)alkenyl, (C2-C10)alkynyl, (C1-C10)alkoxy, (C6-C20)aryloxy, (C3-C7)cycloalkyl, thio(C1-C10)alkyl, (C1-C10)alkylsilyl, (C6-C20)arylsilyl, (C3-C20)heteroaryl, 5- to 7-membered heterocycloalkyl or —$NR^{21}R^{22}$, the $R^{21}$ and $R^{22}$ are each independently (C1-C10)alkyl, (C6-C20)aryl or di(C1-C10)alkylamino;

$R^{15}$ to $R^{18}$ are each independently (C6-C20)aryl, (C6-C20)ar(C1-C10)alkyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, mono or di(C1-C10)alkylamino, (C1-C10)alkylsilyl or (C6-C20)arylsilyl, or $R^{15}$ and $R^{16}$ may be linked by (C3-C10)alkylene or (C3-C10)alkenylene to form a ring; and the aryl, aralkyl, alkyl, alkenyl, alkoxy, aryloxy, cycloalkyl, heteroaryl, heterocycloalkyl of $R^{11}$ to $R^{14}$, and the aryl, aralkyl, alkyl, alkenyl, cycloalkyl, heteroaryl, heterocycloalkyl, alkoxy, aryloxy, mono or dialkylamino, alkylsilyl or arylsilyl of $R^{15}$ to $R^{18}$ may be further substituted with one or more selected from the group consisting of (C1-C10)alkyl, (C2-C10)alkenyl, (C2-C10)alkynyl, (C1-C10)alkoxy, (C6-C20)aryloxy, (C1-C10)alkoxysilyl, 5- to 7-membered heterocycloalkyl, di(C1-C10)alkylamino, di(C2-C10)alkenylamino, di(C2-C10)alkynylamino, and halogen.

In Chemical Formulas 2 to 4, more preferably, $R^{11}$ to $R^{14}$ are each phenyl, benzyl, biphenyl, naphthyl, anthracenyl, mesityl, xylyl, methyl, ethyl, ethenyl, ethynyl, n-propyl, i-propyl, propenyl, propynyl, n-butyl, t-butyl, butenyl, butynyl, methylphenyl, ethylphenyl, methoxyphenyl, ethoxyphenyl, isopropylphenyl, isopropoxyphenyl, t-butylphenyl, cumyl, methoxy, ethoxy, phenoxy, tolyloxy, dimethylaminophenyl, cyclopropyl, cyclobutyl, cyclopentyl, cyclohexyl, methylcyclohexyl, ethylcyclohexyl, isopropylcyclohexyl, dimethylamino, thiomethyl, trimethylsilyl or dimethylhydrazyl;

$R^{15}$ to $R^{18}$ are each independently methyl, ethyl, ethenyl, ethynyl, n-propyl, i-propyl, propenyl, propynyl, n-butyl, t-butyl, i-butyl, butenyl, butynyl, phenyl, benzyl, tolyl, xylyl, methoxymethyl, methoxyethyl, methoxypropyl, butylphenyl, methoxyphenyl, methoxy, ethoxy, phenoxy, trimethoxysilylpropyl, N-morpholinpropyl, methylamino, dimethylamino or trimethylsilyl, or the $R^{15}$ and $R^{16}$ may be linked by propylene, butylene, pentylene, or butenylene to form a 5- to 7-membered ring.

In Chemical Formulas 2 to 4, further more preferably, $R^{11}$ to $R^{14}$ are each phenyl, benzyl, biphenyl, naphthyl, methylphenyl, ethylphenyl, methoxyphenyl, ethoxyphenyl, isopropylphenyl, isopropoxyphenyl, t-butylphenyl, dimethylaminophenyl, methylcyclohexyl, ethylcyclohexyl or isopropylcyclohexyl; and $R^{15}$ to $R^{18}$ are each independently methyl, ethyl, ethenyl, ethynyl, n-propyl, i-propyl, propenyl, propynyl, n-butyl, t-butyl, i-butyl, butenyl, butynyl, phenyl, benzyl, tolyl, xylyl, methoxymethyl, methoxyethyl, methoxypropyl, butylphenyl, methoxyphenyl, methoxy, ethoxy, phenoxy, trimethoxysilylpropyl, N-morpholinpropyl, methylamino, dimethylamino or trimethylsilyl, or the $R^{15}$ and $R^{16}$ may be linked by propylene, butylene, pentylene, or butenylene to form a 5- to 7-membered ring.

The ligand having the P—C—C—P skeleton structure represented by Chemical Formula 2 may be selected from (phenyl)$_2$P—CH(methyl)CH(methyl)-P(phenyl)$_2$, (4-methoxyphenyl)$_2$P—CH(methyl)CH(methyl)-P(4-methoxyphenyl)$_2$. (4-methylphenyl)$_2$P—CH(methyl)CH(methyl)-P(4-methylphenyl)$_2$, (4-ethylphenyl)$_2$P—CH(methyl)CH(methyl)-P(phenyl)$_2$. (2-ethylphenyl)$_2$P—CH(methyl)CH(methyl)-P(2-ethylphenyl)$_2$, (2-isopropylphenyl)$_2$P—CH(methyl)CH(methyl)P-(2-isopropylphenyl)$_2$, (2-methylphenyl)$_2$P—CH(methyl)CH(methyl)P-(2-methylphenyl)$_2$, (2-ethylphenyl)$_2$P—CH(methyl)CH(methyl)-P(phenyl)$_2$, (3-methoxyphenyl)$_2$P—CH(methyl)CH(methyl)-P(3-methoxyphenyl)$_2$, (4-ethoxyphenyl)$_2$P—CH(methyl)CH(methyl)-P(2-ethoxyphenyl)$_2$, (4-dimethylaminophenyl)$_2$P—CH(methyl)CH(methyl)-P(4-dimethylaminophenyl)$_2$. (4-ethylcyclohexyl)$_2$P—CH(methyl)CH(methyl)-P(4-ethylcyclohexyl)$_2$. (2-methoxyphenyl)$_2$P—CH(methyl)CH(methyl)-P(2-methoxyphenyl)$_2$. (2-ethoxyphenyl)$_2$P—CH(methyl)CH(methyl)-P(2-ethoxyphenyl)$_2$, (2-dimethylaminophenyl)$_2$P—CH(methyl)CH(methyl)-P(2-dimethylaminophenyl)$_2$. (2-ethylcyclohexyl)$_2$P—CH(methyl)CH(methyl)-P(2-ethylcyclohexyl)$_2$. (4-ethylphenyl)$_2$P—CH(ethyl)CH(methyl)-P(4-ethylphenyl)$_2$, (4-methoxyphenyl)$_2$P—CH(ethyl)CH(methyl)-P(phenyl)$_2$, (2-ethylphenyl)$_2$P—CH(ethyl)CH(methyl)-P(2-ethylphenyl)$_2$, (4-ethylphenyl)$_2$P—CH(ethyl)CH(ethyl)-P(4-ethylphenyl)$_2$, (phenyl)$_2$P—CH(ethyl)CH(ethyl)-P(phenyl)$_2$, (2-ethylphenyl)$_2$P—CH(ethyl)CH(ethyl)-P(2-ethylphenyl)$_2$, (phenyl)$_2$P—CH(isopropyl)CH(methyl)-P(phenyl)$_2$, (4-methoxyphenyl)$_2$P—CH(isopropyl)CH(methyl)-P(4-methoxyphenyl)$_2$. (4-ethylphenyl)$_2$P—CH(isopropyl)CH(methyl)-P(4-ethylphenyl)$_2$, (2-ethylphenyl)$_2$P—CH(isopropyl)CH(methyl)-P(2-ethylphenyl)$_2$, (phenyl)$_2$P—CH(n-propyl)CH(methyl)-P(phenyl)$_2$, (4-methoxyphenyl)$_2$P—CH(n-propyl)CH(methyl)-P(4-methoxyphenyl)$_2$, (4-ethylphenyl)$_2$P—CH(n-propyl)CH(methyl)-P(4-ethylphenyl)$_2$, (2-ethylphenyl)$_2$P—CH(n-propyl)CH(methyl)-P(2-ethylphenyl)$_2$, (phenyl)$_2$P—CH(isopropyl)CH(ethyl)-P(phenyl)$_2$. (4-methoxyphenyl)$_2$P—CH(isopropyl)CH(ethyl)-P(4-methoxyphenyl)$_2$, (4-ethylphenyl)$_2$P—CH(isopropyl)CH(ethyl)-P(4-ethylphenyl)$_2$, (2-ethylphenyl)$_2$P—CH(isopropyl)CH(ethyl)-P(2-ethylphenyl)$_2$, 1,2-di-(P(phenyl)$_2$)cyclohexane, 1,2-di-(P(4-methoxyphenyl)$_2$)cyclohexane, 1,2-di-(P (4-ethylphenyl)$_2$)cyclohexane, 1,2-di-(P (2-ethylphenyl)$_2$)cyclohexane, 1,2-di-(P(phenyl)$_2$)cyclopentane, 1,2-di-(P(4-methoxyphenyl)$_2$)cyclopentane, 1,2-di-(P(4-ethylphenyl)$_2$)cyclopentane, 1,2-di-(P(2-ethylphenyl)$_2$)cyclopentane, (4-ethylphenyl)$_2$P—CH(dimethylamino)CH(dimethylamino)-P(4-ethylphenyl)$_2$, and (2-ethylphenyl)$_2$P—CH(dimethylamino)CH(dimethylamino)-P(2-ethylphenyl)$_2$, but is not limited thereto.

The ligand having the P—N—P skeleton structure represented by Chemical Formula 3 may be selected from (phenyl)$_2$PN(CH$_2$CH$_2$OCH$_3$)P(phenyl)$_2$, (phenyl)$_2$PN (CH$_2$CH$_2$CH$_2$OCH$_3$)P(phenyl)$_2$, (phenyl)$_2$PN (isopropyl) P (phenyl)$_2$, (phenyl)$_2$PN(methyl)P(phenyl)$_2$, (phenyl)$_2$PN (pentyl)P(phenyl)$_2$, (phenyl)$_2$PN(benzyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-t-butylphenyl)P(phenyl)$_2$, (phenyl)$_2$PN(allyl)P(phenyl)$_2$, (phenyl)$_2$PN [(CH$_2$)$_3$Si (OMe)$_3$]P(phenyl)z, (phenyl)$_2$PN [(CH$_2$)$_3$—N-morpholin]P (phenyl)$_2$, (phenyl)$_2$PN(i-propyl)P(Phenyl)$_2$, (2-naphthyl)$_2$ PN(methyl)P(2-naphthyl)$_2$, (p-biphenyl)$_2$PN(methyl)P(p-biphenyl)$_2$, (m-methylphenyl)$_2$PN(methyl)P(m-methylphenyl)$_2$, (p-methylphenyl)$_2$PN(methyl)P(p-methylphenyl)$_2$. (o-ethylphenyl) (Ph) PN (i-propyl) PPh$_2$, (phenyl)$_2$PN (SiMe$_3$) P (phenyl)$_2$, and (o-methylphenyl)$_2$PN(i-propyl)P (o-methylphenyl)(phenyl), but is not limited thereto.

The ligand having the P—C=C—P skeleton structure represented by Chemical Formula 4 may be selected from 1,2-bis(diphenylphosphino)benzene, 1-methyl-2,3-bis(diphenylphosphino)benzene, 1,2-bis(bis(4-methoxyphenyl) phosphino)benzene, 1,2-bis(bis(4-methylphenyl)phosphino) benzene, 1-(bis(4-ethylphenyl)phosphino)-2-(diphenylphosphino)benzene, 1,2-bis(bis(2-ethylphenyl) phosphino)benzene, 1,2-bis(bis(2-isopropylphenyl) phosphino)benzene, 1,2-bis(bis(2-methylphenyl)phosphino) benzene, 1-(bis(2-ethylphenyl)phosphino)-2-(diphenylphosphino)benzene, 1,2-bis(bis(2-ethylphenyl) phosphino)benzene, 1,2-bis(bis(3-methoxyphenyl) phosphino)benzene, 1-(bis(3-ethoxyphenyl)phosphino)-2-(bis(4-ethoxyphenyl)phosphino)benzene, 1,2-bis(bis(4-dimethylaminophenyl)phosphino)benzene, 1,2-bis(bis(4-ethylcyclohexyl)phosphino)benzene, 1,2-bis(bis(2-methoxyphenyl)phosphino)benzene, 1,2-bis(bis(2-ethoxyphenyl)phosphino)benzene, 1,2-bis(bis(2-dimethylaminophenyl)phosphino)benzene, and 1,2-bis(bis (2-ethylcyclohexyl)phosphino)benzene, but is not limited thereto.

In order to stably maintain the activity of the catalyst and prevent the decrease of the reaction rate as the reaction time elapses, the heteroatom ligand is preferably the ligand having the P—C—C—P skeleton structure represented by Chemical Formula 2 or the ligand having the P—C=C—P skeleton structure represented by Chemical Formula 4, and more preferably the ligand of the P—C—C—P skeleton structure represented by Chemical Formula 2.

In particular, the ligand having the P—C—C—P skeleton structure represented by Chemical Formula 2 or the ligand having the P—C=C—P skeleton structure represented by Chemical Formula 4 includes the phosphorus (P) only as the heteroatom in the skeleton structure of the ligand, and has a structure of two carbons (carbon-carbon) skeleton without nitrogen atom between two phosphorus atoms. By controlling a spatial structure moderately with a substituent around carbon, it is possible to exhibit excellent catalytic activity and to achieve high selectivity of 1-hexene or high selectivity of 1-octene.

The transition metal or transition metal precursor is not particularly limited, but may be a Group 4, Group 5 or Group 6 transition metal, or a precursor thereof, preferably may be selected from chromium, molybdenum, tungsten, titanium, tantalum, vanadium, zirconium, precursors thereof, and more preferably chromium or a chromium precursor.

The chromium precursor is not particularly limited, but is preferably selected from the group consisting of chromium (III) acetylacetonate, chromium (III) chloride tris-tetrahydrofuran, and chromium (III) 2-ethylhexanoate.

The oligomerization catalyst according to the present invention may be a mononuclear or binuclear oligomerization catalyst in which a halogen-substituted organic ligand and a heteroatom ligand coordinate to a transition metal or a transition metal precursor, and specifically may be represented by $ML^1(L^2)_p(X)_q$, or $M_2X^1{}_2L^1{}_2(L^2)_y(X)_z$, wherein M is a transition metal, $L^1$ is a heteroatom ligand, $L^2$ is a halogen-substituted organic ligand, X and $X^1$ are each independently a functional group derived from a transition metal precursor, for example, halogen, p is an integer of 1 or more, q is an integer of (oxidation number of M−p), y is an integer of 2 or more, and z is an integer of (2×oxidation number of M)−2−y.

The oligomerization catalyst according to the present invention may allow to coordinate the heteroatom ligand having the P—C—C—P skeleton structure represented by Chemical Formula 2, the heteroatom ligand having the P—N—P skeleton structure represented by Chemical Formula 3 or the heteroatom ligand having the P—C=C—P skeleton structure represented by Chemical Formula 4 below, preferably the heteroatom ligand having the P—C—C—P skeleton structure represented by Chemical Formula 2 or the heteroatom ligand having the P—C=C—P skeleton structure represented by Chemical Formula 4 below without including nitrogen in the skeleton structure, and more preferably, the heteroatom ligand having the P—C—C—P skeleton structure represented by Chemical Formula 2 without including nitrogen in the skeleton structure, and an enolate-based ligand represented by Chemical Formula 1 with chromium or a chromium precursor, and thus it is possible to improve solubility with respect to an aliphatic hydrocarbon solvent, and to prepare 1-hexene and 1-octene with high activity and high selectivity while stably maintaining oligomerization reaction activity:

[Chemical Formula 1]

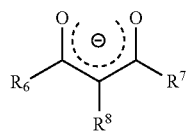

[Chemical Formula 2]

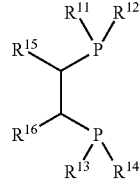

-continued

[Chemical Formula 3]
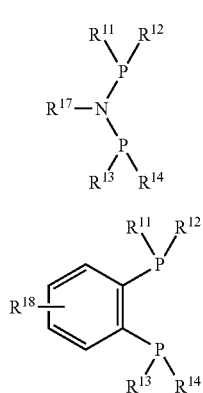

[Chemical Formula 4]

in Chemical Formulas 1 to 4, $R^6$ and $R^7$ are each independently fluorine-substituted (C1-C10)alkyl or fluorine-substituted (C6-C20)aryl, the fluorine-substituted alkyl and the fluorine-substituted aryl of the $R^6$ and $R^7$ may be further substituted with one or more substituents selected from chloro, bromo, (C1—C10)alkyl, (C6-C20)aryl, halo(C1-C10)alkyl, and halo(C6-C20)aryl in addition to fluorine;

$R^8$ is hydrogen, halogen, (C1-C10)alkyl or (C6-C20)aryl; the alkyl and aryl of $R^8$ may be further substituted with one or more of halogen, (C1-C10)alkyl, (C6-C20)aryl, halo(C1-C10)alkyl, and halo(C6-C20)aryl;

$R^6$ and $R^8$ or $R^7$ and $R^8$ may be linked by (C3-C10)alkylene, (C3-C10)alkenylene, (C6-C20)arylene, (C3-C10)heteroalkylene, (C3-C10)heteroalkenylene or (C6-C20)heteroarylene to form a ring;

$R^{11}$ to $R^{14}$ are each independently (C6-C20)aryl, (C6-C20)ar(C1-C10)alkyl, (C1-C10)alkyl, (C2-C10)alkenyl, (C2-C10)alkynyl, (C1-C10)alkoxy, (C6-C20)aryloxy, (C3-C7)cycloalkyl, thio(C1-C10)alkyl, (C1-C10)alkylsilyl, (C6-C20)arylsilyl, (C3-C20)heteroaryl, 5- to 7-membered heterocycloalkyl or —$NR^{21}R^{22}$, the $R^{21}$ and $R^{22}$ are each independently (C1-C10)alkyl, (C6-C20)aryl or di(C1-C10)alkylamino;

$R^{15}$ to $R^{18}$ are each independently (C6-C20)aryl, (C6-C20)ar(C1-C10)alkyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, mono or di(C1-C10)alkylamino, (C1-C10)alkylsilyl or (C6-C20)arylsilyl, or $R^{15}$ and $R^{16}$ may be linked by (C3-C10)alkylene or (C3-C10)alkenylene to form a ring; and the aryl, aralkyl, alkyl, alkenyl, alkoxy, aryloxy, cycloalkyl, heteroaryl, heterocycloalkyl of $R^{11}$ to $R^{14}$, and the aryl, aralkyl, alkyl, alkenyl, cycloalkyl, heteroaryl, heterocycloalkyl, alkoxy, aryloxy, mono or dialkylamino, alkylsilyl or arylsilyl of $R^{15}$ to $R^{18}$ may be further substituted with one or more selected from the group consisting of (C1-C10)alkyl, (C2-C10)alkenyl, (C2-C10)alkynyl, (C1-C10)alkoxy, (C6-C20)aryloxy, (C1-C10)alkoxysilyl, 5- to 7-membered heterocycloalkyl, di(C1-C10)alkylamino, di(C2-C10)alkenylamino, di(C2-C10)alkynylamino, and halogen.

Even more preferably, the oligomerization catalyst according to the present invention may have a complex structure in which the heteroatom ligand having the P—C—C—P skeleton structure represented by Chemical Formula 2 without including nitrogen in the skeleton structure and the enolate-based ligand represented by Chemical Formula 1 coordinate to chromium or a chromium precursor.

The oligomerization catalyst according to the present invention may be specifically exemplified by the following structures, but is not limited thereto:

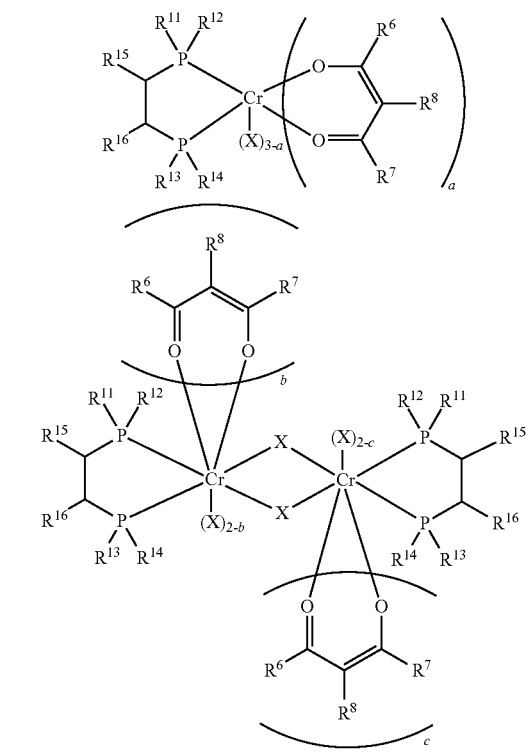

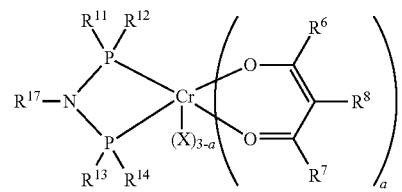

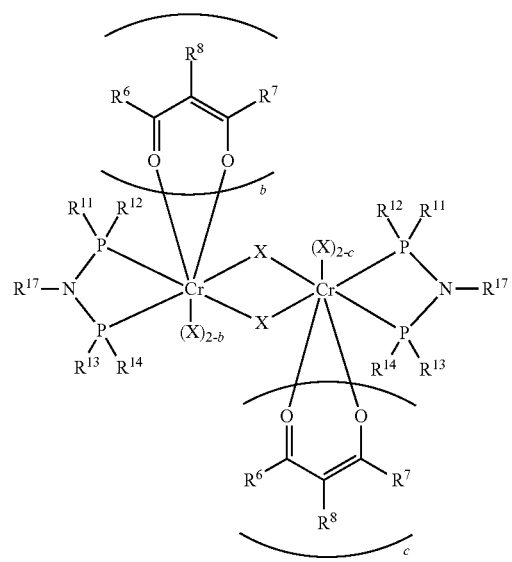

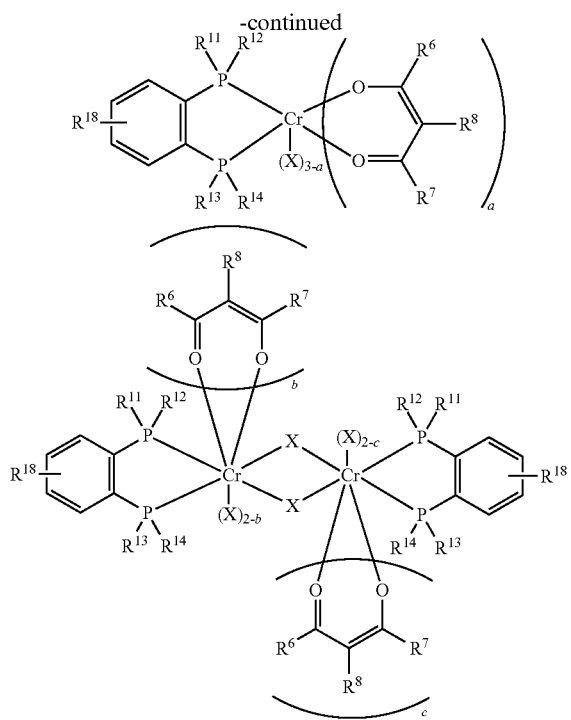

in the above structures, $R^6$ and $R^7$ are each independently fluorine-substituted (C1-C10)alkyl or fluorine-substituted (C6-C20)aryl, the fluorine-substituted alkyl and the fluorine-substituted aryl of the $R^6$ and $R^7$ may be further substituted with one or more substituents selected from chloro, bromo, (C1-C10)alkyl, (C6-C20)aryl, halo(C1-C10)alkyl, and halo(C6-C20)aryl in addition to fluorine;

$R^8$ is hydrogen, halogen, (C1-C10)alkyl or (C6-C20)aryl; the alkyl and aryl of $R^8$ may be further substituted with one or more of halogen, (C1-C10)alkyl, (C6-C20)aryl, halo(C1-C10)alkyl, and halo(C6-C20)aryl;

$R^6$ and $R^8$ or $R^7$ and $R^8$ may be linked by (C3-C10)alkylene, (C3-C10)alkenylene, (C6-C20)arylene, (C3-C10)heteroalkylene, (C3-C10)heteroalkenylene or (C6-C20)heteroarylene to form a ring;

$R^{11}$ to $R^{14}$ are each independently (C6-C20)aryl, (C6-C20)ar(C1-C10)alkyl, (C1-C10)alkyl, (C2-C10)alkenyl, (C2-C10)alkynyl, (C1-C10)alkoxy, (C6-C20)aryloxy, (C3-C7)cycloalkyl, thio(C1-C10)alkyl, (C1-C10)alkylsilyl, (C6-C20)arylsilyl, (C3-C20)heteroaryl, 5- to 7-membered heterocycloalkyl or —$NR^{21}R^{22}$, the $R^{21}$ and $R^{22}$ are each independently (C1-C10)alkyl, (C6-C20)aryl or di(C1-C10)alkylamino;

$R^{15}$ to $R^{18}$ are each independently (C6-C20)aryl, (C6-C20)ar(C1-C10)alkyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6—C20)aryloxy, mono or di(C1-C10)alkylamino, (C1-C10)alkylsilyl or (C6-C20)arylsilyl, or $R^{15}$ and $R^{16}$ may be linked by (C3-C10)alkylene or (C3-C10)alkenylene to form a ring;

the aryl, aralkyl, alkyl, alkenyl, alkoxy, aryloxy, cycloalkyl, heteroaryl, heterocycloalkyl of $R^{11}$ to $R^{14}$, and the aryl, aralkyl, alkyl, alkenyl, cycloalkyl, heteroaryl, heterocycloalkyl, alkoxy, aryloxy, mono or dialkylamino, alkylsilyl or arylsilyl of $R^{15}$ to $R^{18}$ may be further substituted with one or more selected from the group consisting of (C1-C10)alkyl, (C2-C10)alkenyl, (C2-C10)alkynyl, (C1-C10)alkoxy, (C6-C20)aryloxy, (C1-C10)alkoxysilyl, 5- to 7-membered heterocycloalkyl, di(C1-C10)alkylamino, di(C2-C10)alkenylamino, di(C2-C10)alkynylamino, and halogen;

X is halogen; and a is an integer of 1 to 3, and b and c are each independently an integer of 1 or 2.

More preferably, in the above structure, $R^6$ and $R^7$ are each independently fluorine-substituted (C1-C10)alkyl; $R^8$ is hydrogen, fluoro or (C1-C10)alkyl, $R^{11}$ to $R^{14}$ are each phenyl, benzyl, biphenyl, naphthyl, methylphenyl, ethylphenyl, methoxyphenyl, ethoxyphenyl, isopropylphenyl, isopropoxyphenyl, t-butylphenyl, dimethylaminophenyl, methylcyclohexyl, ethylcyclohexyl or isopropylcyclohexyl; $R^{15}$ to $R^{18}$ are each independently methyl, ethyl, ethenyl, ethynyl, n-propyl, i-propyl, propenyl, propynyl, n-butyl, t-butyl, i-butyl, butenyl, butynyl, phenyl, benzyl, tolyl, xylyl, methoxymethyl, methoxyethyl, methoxypropyl, butylphenyl, methoxyphenyl, methoxy, ethoxy, phenoxy, trimethoxysilylpropyl, n-morpholine propyl, methylamino, dimethylamino, or trimethylsilyl, or the $R^{15}$ and $R^{16}$ may be linked by propylene, butylene, pentylene, or butenylene to form a 5- to 7-membered ring.

The halogen-substituted organic ligand and the heteroatom ligand constituting the oligomerization catalyst according to the present invention may be prepared using various methods known to those skilled in the art.

Further, the present invention provides an oligomerization catalyst composition including the oligomerization catalyst of the present invention and a cocatalyst for more effective activity and high selectivity.

In the oligomerization catalyst composition according to the present invention, the oligomerization catalyst composition may be an oligomerization catalyst system including a transition metal or transition metal precursor, a halogen-substituted organic ligand, a heteroatom ligand, and a cocatalyst.

The cocatalyst employed in the oligomerization catalyst composition according to the present invention may be in principle of any compound which activates a transition metal complex in which the halogen-substituted organic ligand and the heteroatom ligand coordinate. The cocatalyst may also be used as a mixture. Compounds that are suitable as the cocatalyst include an organoaluminum compound, an organic boron compound, an organic salt, and the like.

The organoaluminum compound suitable for being used as activator in the oligomerization catalyst composition according to the present invention includes a compound of $AlR_3$ (wherein R is each independently (C1-C12)alkyl, (C6-C20)aryl, (C2-C10)alkenyl, (C2-C10)alkynyl, (C1-C12) alkoxy or halogen), an aluminoxane-based compound or $LiAlH_4$, or the like.

In the oligomerization catalyst composition according to the present invention, as the cocatalyst, one or a mixture of two or more selected from trimethyl aluminum (TMA), triethyl aluminum (TEA), triisobutyl aluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride, and aluminoxane is included.

The aluminoxane is widely known in the art as an oligomeric compound that is capable of being typically prepared by appropriately adding water to an alkylaluminum compound such as trimethylaluminum. The resulting aluminoxane oligomer compound may be linear, cyclic, cage or a mixture thereof.

Examples of suitable organoboron compound may include boroxine, NaBH$_4$, triethylborane, triphenylborane, triphenylborane ammonia complex, tributylborate, triisopropylborate, tris(pentafluorophenyl)borane, triethyl(tetrapentafluorophenyl)borate, dimethylphenylammonium(tetrapentafluorophenyl)borate, diethylphenylammonium (tetrapentafluorophenyl)borate, methyldiphenylammonium (tetrapentafluorophenyl)borate or ethyldiphenylammonium (tetrapentafluorophenyl)borate. These organoboron compounds may be used as a mixture with the organoaluminum compound.

In particular, among the cocatalysts, the aluminoxane may be selected from alkylaluminoxane such as methylaluminoxane (MAO), ethylaluminoxane (EAO), tetraisobutylaluminoxane (TIBAO) and isobutylaluminoxane (IBAO) and modified alkyl aluminoxane such as modified methyl aluminoxane (MAO). The modified methyl aluminoxane (manufactured by Akzo Nobel) contains, in addition to a methyl group, a mixed alkyl group such as isobutyl or n-octyl group.

The cocatalyst is preferably methylaluminoxane (MAO), ethylaluminoxane (EAO), tetraisobutylaluminoxane (TIBAO), or isobutylaluminoxane (IBAO).

In the oligomerization catalyst composition according to the present invention, a ratio of the oligomerization catalyst to the aluminoxane is 1:1 to 10,000:1, more preferably 1:1 to 1,000:1, based on a molar ratio of aluminum to transition metal.

In addition, the present invention provides a method for preparing 1-hexene or 1-octene with high activity and high selectivity from ethylene using the oligomerization catalyst or oligomerization catalyst composition.

The oligomerization catalyst and the cocatalyst, which are individual components of the oligomerization catalyst composition of the present invention, may be blended simultaneously or sequentially in any order in the presence of a solvent to provide an active catalyst. The mixing of the respective catalyst components may be performed at a temperature of −20 to 250° C. and the presence of the olefin during the mixing of the catalyst components may generally exhibit a protective effect and may provide improved catalyst performance. A more preferable temperature range is 20 to 100° C.

The reaction product disclosed herein, in other words, the ethylene oligomer, in particular, 1-hexene or 1-octene, may be prepared by a homogeneous liquid phase reaction in the presence of an inert solvent or a two-phase liquid/liquid reaction, or a bulk phase reaction or a gaseous reaction in which a product olefin acts as a main medium using conventional apparatus and contact techniques with the oligomerization catalyst or oligomerization catalyst composition according to the present invention. However, the homogeneous liquid phase reaction in the presence of an inert solvent is preferred.

The method for preparing the selective oligomer according to the present invention may be performed in an inert solvent. In other words, any inert solvent that does not react with the oligomerization catalyst and the cocatalyst of the present invention may be used, and it is preferable to use aliphatic hydrocarbon as the inert solvent in order to improve a catalytic activity. The oligomerization catalyst system according to the present invention includes halogen, particularly a fluorine-substituted organic ligand, in order to have very high solubility with respect to an aliphatic hydrocarbon solvent, and thus it is easy to control a catalyst amount at the time of continuous introduction of the catalyst solution, and excellent catalytic activity is exhibited.

The aliphatic hydrocarbon is preferably a saturated aliphatic hydrocarbon, and includes linear saturated aliphatic hydrocarbon represented by $C_nH_{2n+2}$ (wherein n is an integer of 1 to 15), alicyclic saturated aliphatic hydrocarbon represented by $C_mH_{2m}$ (wherein m is an integer of to 8), and linear or cyclic saturated aliphatic hydrocarbon in which one or more lower alkyl groups having 1 to 3 carbon atoms are substituted. Specifically, the aliphatic hydrocarbon may be at least one selected from hexane, heptane, octane, nonane, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but is not limited thereto. The saturated aliphatic hydrocarbon is more preferably methylcyclohexane, cyclohexane, hexane or heptane.

The oligomerization reaction according to the present invention may be performed at a temperature of −20 to 250° C. preferably from 15 to 130° C. more preferably from 30 to 70° C. A reaction pressure may be preferably atmospheric pressure to 500 bar, preferably 10 to 70 bar, and more preferably 30 to 50 bar.

From ethylene through the oligomerization reaction according to the preparation method of the present invention, 1-octene may be obtained in an amount of 30 wt % or more, preferably 50 wt % or more, and more preferably 70 wt %. In this case, the yield means a weight percentage (wt %) of 1-octene formed with respect to the total weight of formed 1-hexene and 1-octene.

The method according to the invention may provide, in addition to 1-hexene or 1-octene, 1-butene, 1-hexene, methylcyclopentane, methylene cyclopentane, propyl cyclopentane and a number of high-grade oligomer and polyethylene each in different amount according to oligomerization catalyst and reaction conditions.

The method according to the present method may be performed with a plant including any type of reactor. Examples of the reactor may include, but are not limited to, a batch reactor, a semi-batch reactor and a continuous reactor. The plant may include a reactor in combination with an olefin reactor and an inlet of the oligomerization catalyst composition in the reactor, a line for discharging a oligomerization reaction product from the reactor, and at least one separator for separating the oligomerization reaction product. Here, the catalyst composition may include the oligomerization catalyst disclosed herein and the cocatalyst.

The oligomerization catalyst or the oligomerization catalyst composition according to the present invention may be used to oligomerize ethylene to prepare 1-hexene or 1-octene with high activity and high selectivity.

The following Examples are provided to describe effects of the present invention in detail. However, the following Examples are intended to illustrate the present invention and are not intended to limit the scope of the present invention.

Preparation of Catalyst

[Example 1] Preparation of Oligomerization Catalyst I

Chromium (III) chloride tris-tetrahydrofuran (CrCl$_3$(THF)$_3$) in an amount of 2.1 mg (5.3 µmol) was dissolved in 1 mL of dichloromethane, and then 2.4 mg (5.6 µmol) of (S,S)-(phenyl)$_2$PCH(methyl)CH(methyl)P(phenyl)$_2$ ligand compound dissolved in 1 mL of dichloromethane was slowly added thereto. The reaction product was stirred for additional 5 minutes, and then 1.3 mg (5.6 μmol) of sodium hexafluoroacetylacetonate was slowly added. The reaction product was stirred for further 3 hours and then filtered using a 0.2 μm syringe filter. The filtered liquid was treated in vacuo to remove volatile materials and dried to obtain a dark green solid, which was designated as oligomerization catalyst I. A structure thereof was shown in FIG. 1.

[Example 2] Preparation of Oligomerization Catalyst II

The oligomerization catalyst II was prepared in the same manner as in Example 1 except that 11.2 mg (26.3 μmol) of a (phenyl)$_2$PN(isopropyl)P(phenyl)$_2$ ligand was used instead of 2.4 mg (5.6 μmol) of the (S,S)-(phenyl)$_2$PCH(methyl)CH(methyl)P(phenyl)$_2$ ligand compound of Example 1, an amount of the used chromium (III) chloride tris-tetrahydrofuran (CrCl$_3$(THF)$_3$) was 2.1 mg (5.3 μmol) instead of 9.8 mg (25 μmol), and an amount of the sodium hexafluoroacetylacetonate was 6.0 mg (26.3 μmol) instead of 1.3 mg (5.6 μmol).

[Example 3] Preparation of Oligomerization Catalyst III

An oligomerization catalyst III was prepared in the same manner as in Example 1 except that 2.5 mg (5.6 μmol) of the phenylene 1,2-bis(diphenylphosphine) ligand compound was used instead of 2.4 mg (5.6 μmol) of the (S,S)-(phenyl)$_2$PCH(methyl)CH(methyl)P(phenyl)$_2$ ligand compound of Example 1.

[Example 4] Preparation of Oligomerization Catalyst IV

An oligomerization catalyst IV was prepared in the same manner as in Example 1 except that 2.2 mg (5.6 μmol) of the ethylene bis(diphenylphosphine) ligand compound was used instead of 2.4 mg (5.6 μmol) of the (S,S)-(phenyl)$_2$PCH(methyl)CH(methyl)P(phenyl)$_2$ ligand compound of Example 1.

[Comparative Example 1] Preparation of Comparative Catalyst A

Chromium (III) chloride tris-tetrahydrofuran (CrCl$_3$(THF)$_3$) in an amount of 2.1 mg (5.3 μmol) was dissolved in 1 mL of dichloromethane, and then 2.4 mg (5.6 μmol) of (S,S)-(phenyl)$_2$PCH(methyl)CH(methyl)P(phenyl)$_2$ ligand compound dissolved in 1 mL of dichloromethane was slowly added thereto. The reaction product was further stirred for 5 minutes, and then volatile materials were removed in vacuo to prepare Comparative Catalyst A. A structure thereof was shown in FIG. 1.

[Comparative Example 2] Preparation of Comparative Catalyst B

Comparative Catalyst B was prepared in the same manner as in Comparative Example 1 except that 11.2 mg (26.3 μmol) of the (phenyl)$_2$PN(isopropyl)P(phenyl)$_2$ ligand compound was used instead of 2.4 mg (5.6 μmol) of the (S,S)-(phenyl)$_2$PCH(methyl) CH(methyl) P (phenyl)$_2$ ligand compound of Comparative Example 1, and an amount of the used chromium (III) chloride tris-tetrahydrofuran (CrCl$_3$(THF)$_3$) was 9.8 mg (25 μmol) instead of 2.1 mg (5.3 μmol).

[Comparative Example 3] Preparation of Comparative Catalyst C

Comparative Catalyst C was prepared in the same manner as in Comparative Example 1 except that 2.5 mg (5.6 μmol) of the phenylene 1,2-bis(diphenylphosphine) ligand compound was used instead of 2.4 mg (5.6 μmol) of the (S,S)-(phenyl)$_2$PCH(methyl)CH(methyl)P(phenyl)$_2$ ligand compound of Comparative Example 1.

[Comparative Example 4] Preparation of Comparative Catalyst D

Comparative Catalyst D was prepared in the same manner as in Comparative Example 1 except that 2.2 mg (5.6 μmol) of the ethylene bis(diphenylphosphine) ligand compound was used instead of 2.4 mg (5.6 μmol) of the (S,S)-(phenyl)$_2$PCH(methyl) CH(methyl) P (phenyl)$_2$ ligand compound of Comparative Example 1.

Figure 2:
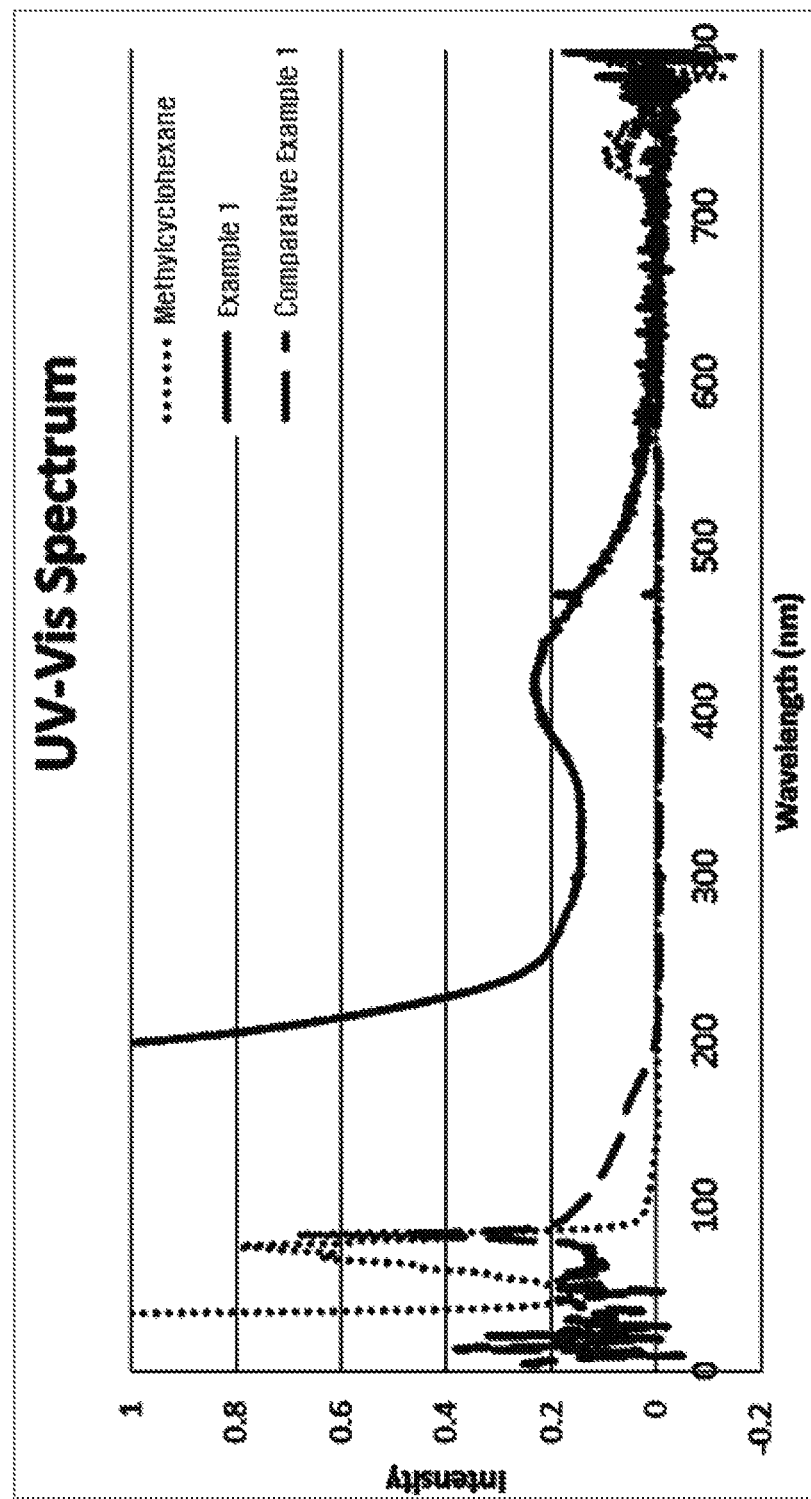
FIG. 2 shows UV-Vis spectra of the catalysts prepared in Example 1 and Comparative Example 1 in methylcyclohexane.

In order to confirm the solubility due to the fluorine-substituted organic ligand in the oligomerization catalyst, the oligomerization catalyst I (10 mg) of Example 1 and the Comparative Catalyst A (10 mg) of Comparative Example 1 were added and dissolved or dispersed in methylcyclohexane (10 mL), respectively, and then the UV-Vis spectrum was measured. Results thereof are shown in FIG. 2. It was confirmed from FIG. 2 that the oligomerization catalyst I of Example 1 was completely dissolved in methylcyclohexane and absorbed light in a visible light wavelength band (380 to 800 nm). On the other hand, it was confirmed that the Comparative Catalyst A of Comparative Example 1 did not absorb light in the visible light wavelength band, and thus the catalyst was not dissolved in methylcyclohexane, but dispersed.

Ethylene Oligomerization Reaction

Example 5

After washing the 2 L stainless steel reactor with nitrogen and vacuum, 1 L of methylcyclohexane was added to the reactor. Modified methylaluminoxane (m-MAO3A, Akzo Nobel, 18 wt % in heptane) (1.57 g) as a cocatalyst was added thereto, and a temperature was raised to 60° C. It was confirmed that the catalyst I (5.3 μmol-Cr) of Example 1 was mixed and dissolved in 10 ml of methylcyclohexane in 50 ml of a Schlenk vessel in a glove box, and added to the reactor. The pressure reactor was charged with 20 bar of ethylene and stirred at a stirring rate of 250 rpm. After 120 minutes, the ethylene feed to the reactor was stopped, the reaction was stopped by stopping stirring, and the reactor was cooled to 10° C or less.

After the excess ethylene was discharged from the reactor, ethanol containing 10 vol % hydrochloric acid was injected into the liquid contained in the reactor. Nonane as an internal standard material was added to analyze the liquid phase by GC-FID. A small amount of organic layer sample was passed over anhydrous magnesium sulfate, dried, and analyzed by GC-FID. The remaining organic layer was filtered to separate a solid wax/polymer product. These solid products were dried overnight in a 100° C oven and weighed to obtain polyethylene. GC analysis was performed to determine a ratio and a generation amount of the reaction mixture, i.e., 1-hexene and 1-octene.

Example 6

The oligomerization reaction was performed in the same manner as in Example 5 except for using a catalyst injection solution in which the catalyst II (5.3 μmol-Cr) instead of the catalyst I (5.3 μmol-Cr) was dissolved in 50 ml of methylcyclohexane.

Example 7

The oligomerization reaction was performed in the same manner as in Example 5 except for using the catalyst III (5.3 μmol-Cr) instead of the catalyst I (5.3 μmol-Cr).

Example 8

The oligomerization reaction was performed in the same manner as in Example 5 except for using the catalyst IV (5.3 μmol-Cr) instead of the catalyst I (5.3 μmol-Cr).

Comparative Example 5

After washing the 2 L stainless steel reactor with nitrogen and vacuum, 1 L of methylcyclohexane was added to the reactor. Modified methylaluminoxane (m-MAO3A, Akzo Nobel, 18 wt % in heptane) (1.57 g) as a cocatalyst was added thereto, and a temperature was raised to 60° C. The catalyst A (5.3 μmol-Cr) of Comparative Example 1 was mixed in 10 ml of methylcyclohexane in 50 ml of a Schlenk vessel in a glove box, quickly stirred so as to prevent the solid from sinking, and added to the reactor. The pressure reactor was charged with 20 bar of ethylene and stirred at a stirring rate of 250 rpm. After 120 minutes, the ethylene feed to the reactor was stopped, the reaction was stopped by stopping stirring, and the reactor was cooled to 10° C. or less.

After the excess ethylene was discharged from the reactor, ethanol containing 10 vol % hydrochloric acid was injected into the liquid contained in the reactor. Nonane as an internal standard material was added to analyze the liquid phase with GC-FID. A small amount of organic layer sample was passed over anhydrous magnesium sulfate, dried, and analyzed by GC-FID. The remaining organic layer was filtered to separate a solid wax/polymer product. These solid products were dried overnight in a 100° C. oven and weighed to obtain polyethylene. GC analysis was performed to determine a ratio and a generation amount of the reaction mixture, i.e., 1-hexene and 1-octene.

Comparative Example 6

The oligomerization reaction was performed in the same manner as in Comparative Example 5 except for using a catalyst injection solution in which the catalyst B (5.3 μmol-Cr) instead of the catalyst A (5.3 μmol-Cr) was dissolved in 50 ml of methylcyclohexane.

Comparative Example 7

The oligomerization reaction was performed in the same manner as in Comparative Example 5 except for using the catalyst C (5.3 μmol-Cr) instead of the catalyst A (5.3 μmol-Cr).

Comparative Example 8

The oligomerization reaction was performed in the same manner as in Comparative Example 5 except for using the catalyst D (5.3 μmol-Cr) instead of the catalyst A (5.3 μmol-Cr).

Comparative Example 9

The oligomerization reaction was performed in the same manner as in Comparative Example 5 except that 10 mL of toluene instead of 10 mL of methylcyclohexane was used as the catalyst injection solvent.

The oligomerization reaction conditions and results are summarized in Table 1 below.

TABLE 1

| | | Example | | | | Comparative Example | | | | |
|---|---|---|---|---|---|---|---|---|---|---|
| | | 5 | 6 | 7 | 8 | 5 | 6 | 7 | 8 | 9 |
| Catalyst injection solution | Catalyst | I | II | III | IV | A | B | C | D | A |
| | Amount of catalyst used (μmol) | 5.3 | 25 | 5.3 | 5.3 | 5.3 | 25 | 5.3 | 5.3 | 5.3 |
| | Solvent | MCH | MCH | MCH | MCH | MCH | MCH | MCH | MCH | Toluene |
| | Amount of solvent used (mL) | 10 | 50 | 10 | 10 | 10 | 50 | 10 | 10 | 10 |
| | State | Dissolved | Dissolved | Dissolved | Dissolved | Not-dissolved | Not-dissolved | Not-dissolved | Not-dissolved | Dissolved |
| | LAO production weight (g, 1-hexene + 1-octene) | 442 | 227 | 181 | 170 | 364 | 162 | 170 | 147 | 251 |
| | 1-hexene/1-octene | 0.86 | 0.30 | 0.51 | 0.57 | 0.78 | 0.30 | 0.46 | 0.51 | 0.77 |
| | Polymer production amount (g) | 0.19 | 0.933 | 0.645 | 1.087 | 0.32 | 1.048 | 0.724 | 0.547 | 0.700 |
| | Activity (Kg/mol-Cr cat hr) | 41713 | 6800 | 24065 | 23999 | 34299 | 4869 | 22804 | 20773 | 23651 |

From the results shown in Table 1, Examples 5 to 8 using the catalysts I to IV of the present invention in the oligomerization reaction of ethylene had excellent catalytic activity as compared to Comparative Examples 5 to 9 using the catalysts A to D. It could be appreciated that this is because the catalysts I to IV of the present invention further included the fluorine-substituted organic ligand in addition to the heteroatom ligand, unlike the catalysts A to D.

In addition, since the catalysts I to IV of the present invention further included the fluorine-substituted organic ligand in addition to the heteroatom ligand, solubility with respect to the aliphatic hydrocarbon compound solvent such as methylcyclohexane was excellent, unlike the catalysts A to D.

Further, as a result of comparing the catalytic activities of Example 5, Comparative Example 5, and Comparative Example 9, Example 5 using the catalyst I further including the fluorine-substituted organic ligand in addition to the heteroatom ligand had the most excellent catalytic activity.

In Example 5 and Comparative Example 9, the oligomerization was performed in the same manner as above using catalyst injection solutions in which the respective catalysts were dissolved in methylcyclohexane and toluene, respectively. However, despite using the catalyst injection solutions in which the respective catalysts were completely dissolved, it was confirmed that the catalytic activity of Example 5 using the catalyst I of the present invention increased about 1.7 times or more as compared with Comparative Example 9.

It could be appreciated from the above results that when the oligomerization reaction of ethylene using the aliphatic hydrocarbon compound such as methylcyclohexane as the polymerization solvent was performed by using the oligomerization catalyst of the present invention which further included the halogen-substituted organic ligand in addition to the heteroatom ligand, the solubility of the catalyst increased and the catalytic activity thereby was significantly improved as compared with the case of using catalysts other than the catalyst of the present invention.

Further, since the oligomerization catalyst of the present invention had an excellent solubility even in the aliphatic hydrocarbon compound solvent such as methylcyclohexane, the catalyst amount could be easily controlled when the catalyst solution was continuously injected during the oligomerization reaction.

INDUSTRIAL APPLICABILITY

Since the oligomerization catalyst according to the present invention further includes the halogen-substituted organic ligand in addition to the heteroatom ligand, when the oligomerization is performed using an aliphatic hydrocarbon compound as a polymerization solvent, the solubility of the catalyst may be higher than that of the conventionally used aromatic hydrocarbon compound, and thus the activity and the selectivity of the oligomerization reaction may be remarkably improved. In particular, the amount of the catalyst used may be reduced due to the high solubility of the catalyst with respect to the aliphatic hydrocarbon compound which increases the ethylene oligomerization activity, and the catalyst amount may be easily controlled when the catalyst solution is continuously supplied for the oligomerization reaction.

In addition, according to the present invention, the oligomer is prepared by using the oligomerization catalyst and simultaneously using the aliphatic hydrocarbon compound as the polymerization solvent instead of the conventionally used aromatic hydrocarbon compound. Thus, not only the operation stability and environmental pollution problem but also human toxicity problem caused by a small amount of residual solvent remaining in the product at the time of preparing the conventional oligomer, and the like, may be remarkably improved, and it is more economical since it is easy to recover the solvent after the polymerization.

The invention claimed is:

1. A mononuclear or binuclear oligomerization catalyst comprising:

a transition metal or transition metal precursor, a halogen-substituted organic ligand, and a heteroatom ligand, wherein the halogen-substituted organic ligand is a monovalent anionic bidentate organic ligand that coordinates to a transition metal through a non-bonding electron pair of a carbon atom or a heteroatom selected from nitrogen, oxygen and sulfur, and wherein the heteroatom ligand is a ligand having a P—C—C—P skeleton structure represented by Chemical Formula 2 below, a ligand having a P—N—P skeleton structure represented by Chemical Formula 3 below, or a ligand having a P—C=C—P skeleton structure represented by Chemical Formula 4 below:

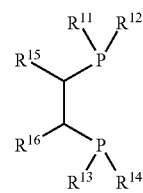

[Chemical Formula 2]

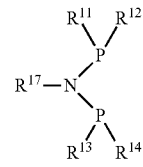

[Chemical Formula 3]

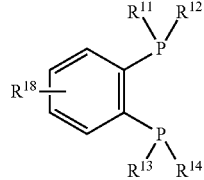

[Chemical Formula 4]

in Chemical Formulas 2 to 4, $R^{11}$ to $R^{14}$ are each independently hydrocarbyl, substituted hydrocarbyl, heterohydrocarbyl, or substituted heterohydrocarbyl;

$R^{15}$ to $R^{16}$ are each independently hydrocarbyl, substituted hydrocarbyl, heterohydrocarbyl, substituted heterohydrocarbyl, or substituted heteroatom; and $R^{17}$ to $R^{18}$ are each independently hydrocarbyl, substituted hydrocarbyl, heterohydrocarbyl, substituted heterohydrocarbyl, or substituted heteroatom, wherein the halogen-substituted organic ligand is selected from the following structures:

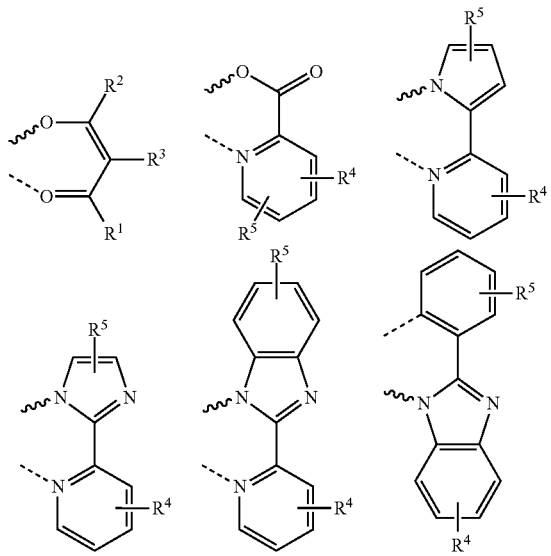

wherein R¹ and R² are each independently halogen, hydrocarbyl, substituted hydrocarbyl, heterohydrocarbyl or substituted heterohydrocarbyl, R³ is hydrogen, halogen, hydrocarbyl, substituted hydrocarbyl, heterohydrocarbyl or substituted heterohydrocarbyl, R¹ and R³ or R² and R³ are optionally linked by hydrocarbylene, substituted hydrocarbylene, heterohydrocarbylene or substituted heterohydrocarbylene to form a ring, provided that at least one of R¹ to R³ is halogen-substituted hydrocarbyl or halogen-substituted heterohydrocarbyl, wherein R⁴ and R⁵ are each independently hydrogen, hydrocarbyl, substituted hydrocarbyl, heterohydrocarbyl or substituted heterohydrocarbyl, provided that at least one of R⁴ and R⁵ is halogen-substituted hydrocarbyl or halogen-substituted heterohydrocarbyl, and wherein the dashed line indicates the non-bonding electron pair and the wave line indicates a bond with the transition metal or transition metal precursor.

2. The mononuclear or binuclear oligomerization catalyst of claim 1, wherein the halogen-substituted organic ligand is an enolate ligand represented by Chemical Formula 1 below:

[Chemical Formula 1]

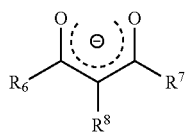

in Chemical Formula 1,

R⁶ and R⁷ are each independently halogen, hydrocarbyl, substituted hydrocarbyl, heterohydrocarbyl or substituted heterohydrocarbyl;

R⁸ is hydrogen, halogen, hydrocarbyl, substituted hydrocarbyl, heterohydrocarbyl, or substituted heterohydrocarbyl;

R⁶ and R⁸ or R⁷ and R⁸ are optionally linked by hydrocarbylene, substituted hydrocarbylene, heterohydrocarbylene or substituted heterohydrocarbylene to form a ring; and at least one of R⁶ to R⁸ is halogen-substituted hydrocarbyl or halogen-substituted heterohydrocarbyl.

3. The mononuclear or binuclear oligomerization catalyst of claim 2, wherein at least one of R⁶ to R⁸ is fluorine-substituted hydrocarbyl or fluorine-substituted heterohydrocarbyl.

4. The mononuclear or binuclear oligomerization catalyst of claim 1, wherein the transition metal or transition metal precursor is a Group 4, Group 5 or Group 6 transition metal, or a precursor thereof.

5. The mononuclear or binuclear oligomerization catalyst of claim 4, wherein the transition metal or transition metal precursor is chromium, molybdenum, tungsten, titanium, tantalum, vanadium, zirconium or a precursor thereof.

6. The mononuclear or binuclear oligomerization catalyst of claim 5, wherein the transition metal or transition metal precursor is a chromium or chromium precursor.

7. The mononuclear or binuclear oligomerization catalyst of claim 6, wherein the chromium precursor is selected from the group consisting of chromium (III) acetylacetonate, chromium (III) chloride tris-tetrahydrofuran, and chromium (III) 2-ethylhexanoate.

8. The mononuclear or binuclear oligomerization catalyst of claim 1, wherein the oligomerization catalyst is a complex in which a chromium or chromium precursor coordinates with an enolate ligand represented by Chemical Formula 1 below, and a ligand having a P—C—C—P skeleton structure represented by Chemical Formula 2 below, a ligand having a P—N—P skeleton structure represented by Chemical Formula 3 below, or a ligand having a P—C=C—P skeleton structure represented by Chemical Formula 4 below:

[Chemical Formula 1]

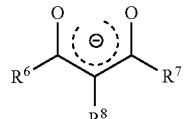

[Chemical Formula 2]

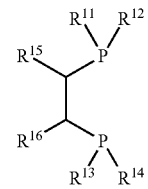

[Chemical Formula 3]

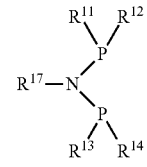

[Chemical Formula 4]

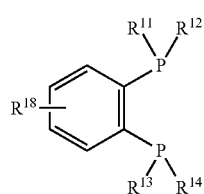

in Chemical Formulas 1 to 4,

R⁶ and R⁷ are each independently fluorine-substituted (C1-C10)alkyl or fluorine-substituted (C6-C20)aryl, the fluorine-substituted alkyl and the fluorine-substituted aryl of R⁶ and R⁷ are optionally further substituted with one or more substituents selected from chloro, bromo, (C1-C10)alkyl, (C6-C20)aryl, halo(C1-C10)alkyl, and halo(C6-C20)aryl in addition to fluorine;

$R^8$ is hydrogen, halogen, (C1-C10)alkyl or (C6-C20)aryl; the alkyl and aryl of $R^8$ are optionally further substituted with one or more of halogen, (C1-C10)alkyl, (C6-C20)aryl, halo(C1-C10)alkyl, and halo(C6-C20)aryl;

$R^6$ and $R^8$ or $R^7$ and $R^8$ are optionally linked by (C3-C10)alkylene, (C3-C10)alkenylene, (C6-C20)arylene, (C3-C10)heteroalkylene, (C3-C10)heteroalkenylene or (C6-C20)heteroarylene to form a ring;

$R^{11}$ to $R^{14}$ are each independently (C6-C20)aryl, (C6-C20)aryl(C1-C10)alkyl, (C1-C10)alkyl, (C2-C10)alkenyl, (C2-C10)alkynyl, (C1-C10)alkoxy, (C6-C20)aryloxy, (C3-C7)cycloalkyl, thio(C1-C10)alkyl, (C1-C10)alkylsilyl, (C6-C20)arylsilyl, (C3-C20)heteroaryl, 5- to 7-membered heterocycloalkyl or —$NR^{21}R^{22}$, the $R^{21}$ and $R^{22}$ are each independently (C1-C10)alkyl, (C6-C20)aryl or di(C1-C10)alkylamino;

$R^{15}$ to $R^{18}$ are each independently (C6-C20)aryl, (C6-C20)aryl(C1-C10)alkyl, (C1-C10)alkyl, (C2-C10)alkenyl, (C2-C10)alkynyl, (C3-C7)cycloalkyl, (C3-C20)heteroaryl, 5- to 7-membered heterocycloalkyl, (C1-C10)alkoxy, (C6-C20)aryloxy, mono or di(C1-C10)alkylamino, (C1-C10)alkylsilyl or (C6-C20)arylsilyl; and the aryl, aralkyl, alkyl, alkenyl, alkoxy, aryloxy, cycloalkyl, heteroaryl, heterocycloalkyl of $R^{11}$ to $R^{14}$, and the aryl, aralkyl, alkyl, alkenyl, cycloalkyl, heteroaryl, heterocycloalkyl, alkoxy, aryloxy, mono or dialkylamino, alkylsilyl or arylsilyl of $R^{15}$ to $R^{18}$ are optionally further substituted with one or more selected from the group consisting of (C1-C10)alkyl, (C2-C10)alkenyl, (C2-C10)alkynyl, (C1-C10)alkoxy, (C6-C20)aryloxy, (C1-C10)alkoxysilyl, 5- to 7-membered heterocycloalkyl, di(C1-C10)alkylamino, di(C2-C10)alkenylamino, di(C2-C10)alkynylamino, and halogen.

9. A method for preparing an ethylene oligomer using a catalyst composition including the mononuclear or binuclear oligomerization catalyst of claim 1 and a cocatalyst.

10. The method of claim 9, wherein the cocatalyst is an organoaluminum compound, an organoboron compound, an organic salt, or a mixture thereof.

11. The method of claim 10, wherein the cocatalyst is one or a mixture of two or more selected from the group consisting of methyl aluminoxane (MAO), modified methyl aluminoxane (MMAO), ethyl aluminoxane (EAO), tetraisobutyl aluminoxane (TIBAO), isobutyl aluminoxane (IBAO), trimethyl aluminum (TMA), triethyl aluminum (TEA), triisobutyl aluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride.

12. The method of claim 9, further comprising using an aliphatic hydrocarbon as a reaction solvent.

13. The method of claim 12, wherein the aliphatic hydrocarbon is at least one selected from hexane, heptane, octane, nonane, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,3-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane.

14. The method of claim 9, wherein the ethylene oligomer includes 1-octene in an amount of 30 wt % or more.

15. The method of claim 14, wherein the ethylene oligomer includes 1-octene in an amount of 50 wt % or more.

16. An oligomerization catalyst comprising:

a transition metal or transition metal precursor, a halogen-substituted organic ligand, and a heteroatom ligand, wherein the transition metal or transition metal precursor is a Group 4, Group 5 or Group 6 transition metal, or a precursor thereof, and wherein the heteroatom ligand is a ligand having a P—C—C—P skeleton structure represented by Chemical Formula 2 below, a ligand having a P—N—P skeleton structure represented by Chemical Formula 3 below, or a ligand having a P—C=C—P skeleton structure represented by Chemical Formula 4 below:

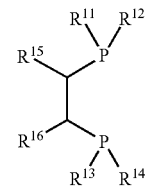

[Chemical Formula 2]

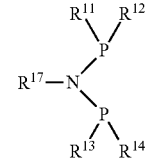

[Chemical Formula 3]

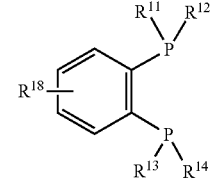

[Chemical Formula 4]

in Chemical Formulas 2 to 4, $R^{11}$ to $R^{14}$ are each independently hydrocarbyl, substituted hydrocarbyl, heterohydrocarbyl or substituted heterohydrocarbyl;

$R^{15}$ to $R^{16}$ are each independently hydrocarbyl, substituted hydrocarbyl, heterohydrocarbyl, substituted heterohydrocarbyl, or substituted heteroatom; and $R^{17}$ to $R^{18}$ are each independently hydrocarbyl, substituted hydrocarbyl, heterohydrocarbyl, substituted heterohydrocarbyl, or substituted heteroatom, wherein the halogen-substituted organic ligand is selected from the following structures:

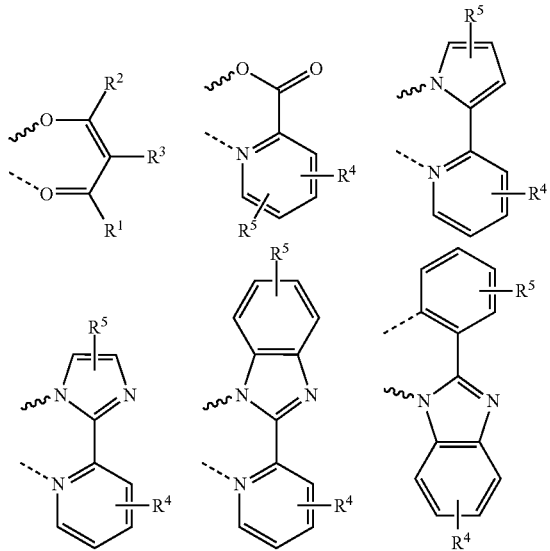

wherein $R^1$ and $R^2$ are each independently halogen, hydrocarbyl, substituted hydrocarbyl, heterohydrocarbyl or substituted heterohydrocarbyl, $R^3$ is hydrogen, halogen, hydrocarbyl, substituted hydrocarbyl, heterohydrocarbyl or substituted heterohydrocarbyl, $R^1$ and $R^3$ or $R^2$ and $R^3$ are optionally linked by hydrocarbylene, substituted hydrocarbylene, heterohydrocarbylene or substituted heterohydrocarbylene to form a ring, provided that at least one of $R^1$ to $R^3$ is halogen-substituted hydrocarbyl or halogen-substituted heterohydrocarbyl, wherein $R^4$ and $R^5$ are each independently hydrogen, hydrocarbyl, substituted hydrocarbyl, heterohydrocarbyl or substituted heterohydrocarbyl, provided that at least one of $R^4$ and $R^5$ is halogen-substituted hydrocarbyl or halogen-substituted heterohydrocarbyl, and wherein the dashed line indicates the non-bonding electron pair and the wave line indicates a bond with the transition metal or transition metal precursor.

\* \* \* \* \*